US005856088A

United States Patent [19]
McDonough et al.

[11] Patent Number: 5,856,088
[45] Date of Patent: Jan. 5, 1999

[54] DETECTION OF HUMAN IMMUNODEFICIENCY VIRUS TYPE 1

[75] Inventors: Sherrol H. McDonough, San Diego; Thomas B. Ryder, Escondido; Yeasing Yang, San Diego, all of Calif.

[73] Assignee: Gen-Probe Incorporated, San Diego, Calif.

[21] Appl. No.: 462,646

[22] Filed: Jun. 5, 1995

Related U.S. Application Data

[63] Continuation of Ser. No. 40,745, Mar. 26, 1993, abandoned, which is a continuation-in-part of Ser. No. 379,501, Jul. 11, 1989, abandoned, and Ser. No. 550,837, Jul. 10, 1990, Pat. No. 5,480,784.

[51] Int. Cl.$^6$ .............................. C12Q 1/70; C12Q 1/68; C07H 21/04; C07H 21/02

[52] U.S. Cl. .......................... 435/5; 536/24.3; 536/24.32; 435/6; 935/77; 935/78

[58] Field of Search ................................ 536/22.1, 24.3, 536/24.32; 435/5, 6

[56] References Cited

U.S. PATENT DOCUMENTS

| | | | |
|---|---|---|---|
| 4,851,330 | 7/1989 | Kohne | 435/6 |
| 5,008,182 | 4/1991 | Sninsky et al. | 435/6 |
| 5,030,557 | 7/1991 | Hogan et al. | 435/6 |
| 5,079,351 | 1/1992 | Sninsky et al. | 435/6 |
| 5,156,949 | 10/1992 | Luciw et al. | 435/6 |
| 5,166,195 | 11/1992 | Ecker | 435/6 |

FOREIGN PATENT DOCUMENTS

| | | |
|---|---|---|
| 0185444 | 6/1986 | European Pat. Off. . |
| 0370694 | 11/1989 | European Pat. Off. . |
| 0403333 | 12/1990 | European Pat. Off. . |
| 0408295 | 1/1991 | European Pat. Off. . |
| 0435150 | 7/1991 | European Pat. Off. . |
| 0469610 | 2/1992 | European Pat. Off. . |
| 0511712 | 11/1992 | European Pat. Off. . |
| 0516540 | 12/1992 | European Pat. Off. . |
| 0519338 | 12/1992 | European Pat. Off. . |
| 0525882 | 2/1993 | European Pat. Off. . |
| 0591914 | 4/1994 | European Pat. Off. . |
| 9307259 | 4/1958 | WIPO . |
| 8801302 | 2/1988 | WIPO . |
| 8904375 | 5/1989 | WIPO . |
| 9008440 | 8/1990 | WIPO . |
| 9108308 | 6/1991 | WIPO . |
| 9110746 | 7/1991 | WIPO . |
| 9200384 | 1/1992 | WIPO . |
| 9201814 | 2/1992 | WIPO . |
| 9202638 | 2/1992 | WIPO . |
| 9216659 | 10/1992 | WIPO . |
| 9222641 | 12/1992 | WIPO . |
| 9300447 | 1/1993 | WIPO . |
| 9302215 | 4/1993 | WIPO . |
| 9313223 | 8/1993 | WIPO . |
| 9325707 | 12/1993 | WIPO . |
| 9403635 | 2/1994 | WIPO . |

OTHER PUBLICATIONS

Agius et al., "Variable Stringency Hybridization of Polymerase Chain Reaction Amplified HIV–1 DNA Fragments," *Journal of Virological Methods* 30:141 (1990).

Albert and Fenyo, "Simple, Sensitive, and Specific Detection of Human Immunodeficiency Virus Type 1 in Clinical Specimens by Polymerase Chain Reaction with Nested Primers," *Journal of Clinical Microbiology* 28:1560 (1990).

Bell and Ratner, "Specificity of Polymerase Chain Amplification Reactions for Human Immunodeficiency Virus Type 1 DNA Sequences," *AIDS Research and Human Retroviruses* 5:87 (1989).

Bruisten et al., "Enhanced Detection of HIV–1 Sequences Using Polymerase Chain Reaction and a Liquid Hybridization Technique," *Vox Sang* 61:24 (1991).

Clarke et al., "Detection of HIV–1 in Human Lung Macrophages Using the Polymerase Chain Reaction," *AIDS* 4:1133–1136 (1990).

Clarke et al., "Human T–cell Leukaemia Virus Type 2," *Nature* 305–60–62 (1983).

Coutlee et al., "Immunodetection of DNA with Biotinylated RNA Probes: A Stuyd of Reactivity of a Monoclonal Antibody to DNA–RNA Hybrids," *Analytical Biochemistry* 181:96 (1989).

Dahlen et al., "Detection of Human Immunodeficiency Virus Type 1 by Using the Polymerase Chain Reaction and a Time–Resolved Fluorescence–Based Hybridization Assay," *Journal of Clinical Microbiology* 29:798–804 (1991).

Dudding et al., "Endoribonucleolytic Cleavage of RNA: Oligodeoxynucleotide Hybrids by the Ribonuclease H Activity of HIV–1 Reverse Transcriptase," *Biochemical and Biophysical Research Communications* 167:244–250 (1990).

Ferrer–Le–Coeur et al., "No Evidence of HIV–1 Infection in Seronegative Hemophiliacs and in Seronegative Partners of Seropositive Hemophiliacs through Polymerase Chain Reaction (PCR) and Anti–NEF Serology," *Thrombosis and Haemostasis* 65:478–482 (1991).

Goswami et al., "Expression of HIV–1 in the Cerebrospinal Fluid Detected by the Polymerase Chain Reaction and its Correlation with Central Nervous System Disease," *AIDS* 5:797–803 (1991).

Grankvist et al., "Selection of Primers of Optimal Sensitivity for the Detection of HIV–1 from Africa and Europe by Polymerase Chain Reaction," *AIDS* 5:474–578 (1991).

Guatelli et al., "Alternative Splice Acceptor Utilization during Human Immunodeficiency Virus Type 1 Infection of Cultured Cells," *Journal of Virology* 64:4093–4098 (1990).

Hart et al., "Direct Detection of HIV RNA Expression in Seropositive Subjects," *The Lancet* 10:596–599 (1988).

Holland et al., "Detection of Specific Polymerase Chain Reaction Product by Utilizing the 5'–3' Exonuclease Activity of *Thermus Aquaticus* DNA Polymerase," *Proc. Natl. Acad. Sci. USA* 88:7276–7280 (1991).

Keller at al., "A Sensitive Nonisotopic Hybridization Assay for HIV–1 DNA," *Analytical Biochemistry* 177:27–32 (1989).

(List continued on next page.)

*Primary Examiner*—Stephanie W. Zitomer
*Attorney, Agent, or Firm*—Lyon & Lyon LLP

[57] ABSTRACT

Amplification oligonucleotides and hybridization assay probes which distinguish Human Immunodeficiency Virus type from other viruses.

89 Claims, No Drawings

OTHER PUBLICATIONS

Kumar et al., "A Method for the Rapid Screening of Human Blood Samples for the Presence of HIV–1 Sequences: The Probe–Shift Assay," *AIDS Research and Human Retroviruses* 5:345–354 (1989).

Kwoh et al., "Transcription–based amplification system and detection of amplified human immunodeficiency virus type 1 with a bead–based sandwich hybridization format," *Proc. Natl. Acad. Sci. USA* 86:1173–1177 (1989).

Kwok et al., "Identification of Human Immunodeficiency Virus Sequences by Using In Vitro Enzymatic Amplification and Oligomer Cleavage Detection," *Journal of Virology* 61:1690–1694 (1987).

Linz et al., "Systematic on Parameters Influencing the Performance of the Polymerase Chain Reaction," *J. Clin. Chem. Clin. Biochem.* 28:5–13 (1990).

Mano and Chermann, "Replication of Human Immunodeficiency Virus Type 1 in Primary Cultured Placental Cells," *Res. Virol.* 142:95–104 (1991).

Mariotti et al., "DNA Amplification of HIV–1 in Seropositive Individuals and in Seronegative At–risk Individuals," *AIDS* 4:633–637 (1990).

Mariotti et al., "Failure to Detect Evidence of Human Immunodeficiency Virus type 1 (HIV–1) Infection by Polymerase Chain Reaction Assay in Blood Donors wit Isolated Core Antibodies (Anti–p24 or –p17) to HIV–1," *Transfusion* 30:704–706 (1990).

Meyerhans et al., "Temporal Fluctuations in HIV Quasispecies in Vivo Are Not Reflected by Sequential HIV Isolations," *Cell* 58:901–910 (1989).

Mousset et al., "Isolation of HIV–1 from Seropositive People Living in Cotonou, Benin," *AIDS* 4:1225–1230 (1990).

Ou et al., "DNA Amplification for Direct Detection of HIV–1 in DNA of Peripheral Blood Mononuclear Cells," *Science* 239:295–297 (1988).

Pang et al., "High Levels of Unintegrated HIV–1 DNA in Brain Tissue of AIDS Demetia Patients," *Nature* 343:85–89 (1990).

Paterlini et al., "Polymerase Chain Reaction for Studies of Mother to Child Transmission of HIV1 in Africa," *Journal of Medical Virology* 30:53–57 (1990).

Perrin et al., "Human Immunodeficiency Virus DNA Amplification and Serology in Blood Donors," *Blood* 76:641–645 (1990).

Preston et al., "Detection of Nucleic Acids Homologous to Human Immunodeficiency Virus in Wastewater," *Journal of Virological Methods* 33:383–390 (1991).

Pritchard and Stefano, "Amplified Detection of Viral Nucleic Acid at Subattomole Levels Using Q Beta Replicase," *Ann. Biol. Clin.* 48:492–497 (1990).

Ratner et al., "Complete Nucleotide Sequence of the AIDS Virus, HTLV–III," *Nature* 313:277 (1985).

Rudin et al., "Repeated Polymerase Chain Reaction Complementary to Other Conventional Methods for Early Detection of HIV Infection in Infants Born to HIV–Infected Mothers," *Eur. J. Clin. Microbiol. Infect. Dis.* 10:146–156 (1991).

Shaw et al., "Molecular Characterization of Human T–Cell Leukemia (Lymphotropic) Virus Type III in the Acquired Immune Deficiency Syndrome," *Science* 226:1165 (1984).

Shimotohno et al., "Complete Nucleotide Sequence of an Infectious Clone of Human T–cell Leukemia Virus Type II: An Open Reading Frame for the Protease Gene," *Proc. Natl. Acad. Sci. USA* 82:3101 (1985).

Shoebridge et al., "Assessment of HIV Status Using the Polymerase Chain Reaction in Antibody–positive Patients and High–risk Antibody–negative Haemophiliacs," *AIDS* 5:221–224 (1991).

Stevenson et al., "Cloning and Characterization of Human Immunodeficiency Virus Type 1 Variants Diminished in the Ability to Induce Syncytium–Independent Cytolysis," *Journal of Virology* 64:3792–3803 (1990).

Truckenmiller et al., "Evidence for Dual Infection of Rabbits with the Human Retroviruses HTLV–I and HIV–1," *Res. Immunol.* 140:527–544 (1989).

Van de Perre et al., "Postnatal Transmission of Human Immunodeficiency Virus Type 1 From Mother to Infant," *The New England Journal of Medicine* 325:593–598 (1991).

Varas et al., "Influence of PCR Parameters on Amplifications of HIV–1 DNA: Establishment of Limiting Sensitivity," *BioTechniques* 11:384–391 (1991).

Velpandi et al., "Generation of Hybrid Human Immunodeficiency Virus Utilizing the Cotransfection Method and Analysis of Cellular Tropism," *Journal of Virology* 65:4847–4852 (1991).

Williams et al., "The Polymerase Chain Reaction in the Diagnosis of Vertically Transmitted HIV Infection," *AIDS* 4:393–398 (1990).

Zachar et al., "Enhanced Chemiluminescence–based Hybridization Analysis for PCR–mediated HIV–1 DNA Detection Offers an Alternative to $^{32}$P–labelled Probes," *Journal of Virological Methods* 133:391–395 (1991).

Zack et al., "HIV–1 Entry into Quiescent Primary Lymphocytes: Molecular Anlaysis Reveals a Labile, Latent Viral Structure," *Cell* 61:213–222 (1990).

Zagury et al., "Genetic Variability Between Isolates of Human Immunodeficiency Virus (HIV) Type 2 is Comparable to the Variability Among HIV Type 1," *Proc. Natl. Acad. Sci. USA* 85:5941 (1988).

SEQUENCE LISTING ( 1 ) GENERAL INFORMATION:

( i i i ) NUMBER OF SEQUENCES: 139

( 2 ) INFORMATION FOR SEQ ID NO: 1:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( i i ) SEQUENCE DESCRIPTION: SEQ ID NO: 1:

GACTAGCGGA GGCTAGAAGG AGAGAGATGG G    3 1

( 2 ) INFORMATION FOR SEQ ID NO: 2:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( i i ) SEQUENCE DESCRIPTION: SEQ ID NO: 2:

GAAGGCTTTC AGCCCAGAAG TAATACCCAT G        31

( 2 ) INFORMATION FOR SEQ ID NO: 3:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) SEQUENCE DESCRIPTION: SEQ ID NO: 3:

ATTTGCATGG CTGCTTGATG TCCCCCCACT        30

( 2 ) INFORMATION FOR SEQ ID NO: 4:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO: 4:

CTTCCCCTTG GTTCTCTCAT CTGGCC        26

( 2 ) INFORMATION FOR SEQ ID NO: 5:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( i i ) SEQUENCE DESCRIPTION: SEQ ID NO: 5:

GTCATCCATC CTATTTGTTC CTGAAGGGTA CTAGTAG        37

( 2 ) INFORMATION FOR SEQ ID NO: 6:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( i i ) SEQUENCE DESCRIPTION: SEQ ID NO: 6:

CTCCCTGACA TGCTGTCATC ATTTCTTCTA GTG        33

( 2 ) INFORMATION FOR SEQ ID NO: 7:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( i i ) SEQUENCE DESCRIPTION: SEQ ID NO: 7:

GTGGAAGCAC ATTGTACTGA TATCTAATCC C        31

( 2 ) INFORMATION FOR SEQ ID NO: 8:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( i i ) SEQUENCE DESCRIPTION: SEQ ID NO: 8:

GCTCCTCTAT TTTTGTTCTA TGCTGCCCTA TTTCTAA 37

( 2 ) INFORMATION FOR SEQ ID NO: 9:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) SEQUENCE DESCRIPTION: SEQ ID NO: 9:

CCTTTGTGTG CTGGTACCCA TGC 23

( 2 ) INFORMATION FOR SEQ ID NO: 10:

( i ) SEQUENCE CHARACTERISTICS:
        ( A ) LENGTH: 29
        ( B ) TYPE: nucleic acid
        ( C ) STRANDEDNESS: single
        ( D ) TOPOLOGY: linear ( i i ) SEQUENCE DESCRIPTION: SEQ ID NO: 10:

CTACTATTCT TTCCCCTGCA CTGTACCCC 29

( 2 ) INFORMATION FOR SEQ ID NO: 11:

( i ) SEQUENCE CHARACTERISTICS:
        ( A ) LENGTH: 29
        ( B ) TYPE: nucleic acid
        ( C ) STRANDEDNESS: single
        ( D ) TOPOLOGY: linear ( i i ) SEQUENCE DESCRIPTION: SEQ ID NO: 11:

AAAGCCTTAG GCATCTCCTA TGGCAGGAA 29

( 2 ) INFORMATION FOR SEQ ID NO: 12:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( i i ) SEQUENCE DESCRIPTION: SEQ ID NO: 12:

GCAGCTGCTT ATATGCAGGA TCTGAGGG 28

( 2 ) INFORMATION FOR SEQ ID NO: 13:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( i i ) SEQUENCE DESCRIPTION: SEQ ID NO: 13:

CAAGGCAAGC TTTATTGAGG CTTAAGCAGT GGG 33

( 2 ) INFORMATION FOR SEQ ID NO: 14:

( i ) SEQUENCE CHARACTERISTICS:
    ( A ) LENGTH: 28
    ( B ) TYPE: nucleic acid
    ( C ) STRANDEDNESS: single
    ( D ) TOPOLOGY: linear ( i i ) SEQUENCE DESCRIPTION: SEQ ID NO: 14:

ATCTCTAGCA GTGGCGCCCG AACAGGGA      28

( 2 ) INFORMATION FOR SEQ ID NO: 15:

( i ) SEQUENCE CHARACTERISTICS:
    ( A ) LENGTH: 24
    ( B ) TYPE: nucleic acid
    ( C ) STRANDEDNESS: single
    ( D ) TOPOLOGY: linear ( i i ) SEQUENCE DESCRIPTION: SEQ ID NO: 15:

TGCGAGAGCG TCAGTATTAA GCGG      24

( 2 ) INFORMATION FOR SEQ ID NO: 16:

( i ) SEQUENCE CHARACTERISTICS:
    ( A ) LENGTH: 36
    ( B ) TYPE: nucleic acid
    ( C ) STRANDEDNESS: single
    ( D ) TOPOLOGY: linear ( i i ) SEQUENCE DESCRIPTION: SEQ ID NO: 16:

CTACTTTGGA ATATTGCTGG TGATCCTTTC CATCCC      36

( 2 ) INFORMATION FOR SEQ ID NO: 17:

( i ) SEQUENCE CHARACTERISTICS:
    ( A ) LENGTH: 33
    ( B ) TYPE: nucleic acid
    ( C ) STRANDEDNESS: single
    ( D ) TOPOLOGY: linear ( i i ) SEQUENCE DESCRIPTION: SEQ ID NO: 17:

CCAATCCCCC CTTTTCTTTT AAAATTGTGG ATG      33

( 2 ) INFORMATION FOR SEQ ID NO: 18:

( i ) SEQUENCE CHARACTERISTICS:
    ( A ) LENGTH: 24
    ( B ) TYPE: nucleic acid
    ( C ) STRANDEDNESS: single
    ( D ) TOPOLOGY: linear ( i i ) SEQUENCE DESCRIPTION: SEQ ID NO: 18:

CTCGCCACTC CCCAGTCCCG CCCA      24

( 2 ) INFORMATION FOR SEQ ID NO: 19:

( i ) SEQUENCE CHARACTERISTICS:
    ( A ) LENGTH: 24
    ( B ) TYPE: nucleic acid
    ( C ) STRANDEDNESS: single
    ( D ) TOPOLOGY: linear ( i i ) SEQUENCE DESCRIPTION: SEQ ID NO: 19:

CTCGACGCAG GACTCGGCTT GCTG      24

( 2 ) INFORMATION FOR SEQ ID NO: 20:

( i ) SEQUENCE CHARACTERISTICS:
    ( A ) LENGTH: 23

( B ) TYPE: nucleic acid
( C ) STRANDEDNESS: single
( D ) TOPOLOGY: linear ( i i ) SEQUENCE DESCRIPTION: SEQ ID NO: 20:

CTCCCCCGCT TAATACTGAC GCT    23

( 2 ) INFORMATION FOR SEQ ID NO: 21:

( i ) SEQUENCE CHARACTERISTICS:
( A ) LENGTH: 31
( B ) TYPE: nucleic acid
( C ) STRANDEDNESS: single
( D ) TOPOLOGY: linear ( i i ) SEQUENCE DESCRIPTION: SEQ ID NO: 21:

GGCAAATGGT ACATCAGGCC ATATCACCTA G    31

( 2 ) INFORMATION FOR SEQ ID NO: 22:

( i ) SEQUENCE CHARACTERISTICS:
( A ) LENGTH: 25
( B ) TYPE: nucleic acid
( C ) STRANDEDNESS: single
( D ) TOPOLOGY: linear ( i i ) SEQUENCE DESCRIPTION: SEQ ID NO: 22:

GGGGTGGCTC CTTCTGATAA TGCTG    25

( 2 ) INFORMATION FOR SEQ ID NO: 23:

( i ) SEQUENCE CHARACTERISTICS:
( A ) LENGTH: 26
( B ) TYPE: nucleic acid
( C ) STRANDEDNESS: single
( D ) TOPOLOGY: linear ( i i ) SEQUENCE DESCRIPTION: SEQ ID NO: 23:

CAGAAGGAGC CACCCCACAA GATTTA    26

( 2 ) INFORMATION FOR SEQ ID NO: 24:

( i ) SEQUENCE CHARACTERISTICS:
( A ) LENGTH: 27
( B ) TYPE: nucleic acid
( C ) STRANDEDNESS: single
( D ) TOPOLOGY: linear ( i i ) SEQUENCE DESCRIPTION: SEQ ID NO: 24:

GACCATCAAT GAGGAAGCTG CAGAATG    27

( 2 ) INFORMATION FOR SEQ ID NO: 25:

( i ) SEQUENCE CHARACTERISTICS:
( A ) LENGTH: 25
( B ) TYPE: nucleic acid
( C ) STRANDEDNESS: single
( D ) TOPOLOGY: linear ( i i ) SEQUENCE DESCRIPTION: SEQ ID NO: 25:

CCCATTCTGC AGCTTCCTCA TTGAT    25

( 2 ) INFORMATION FOR SEQ ID NO: 26:

( i ) SEQUENCE CHARACTERISTICS:
( A ) LENGTH: 19
( B ) TYPE: nucleic acid
( C ) STRANDEDNESS: single ( D ) TOPOLOGY: linear ( i i ) SEQUENCE DESCRIPTION: SEQ ID NO: 26:

AGTGACATAG CAGGAACTA 19

( 2 ) INFORMATION FOR SEQ ID NO: 27:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO: 27:

CCATCCTATT TGTTCCTGAA GGGTAC 26

( 2 ) INFORMATION FOR SEQ ID NO: 28:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) SEQUENCE DESCRIPTION: SEQ ID NO: 28:

AGATTTCTCC TACTGGGATA GGT 23

( 2 ) INFORMATION FOR SEQ ID NO: 29:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) SEQUENCE DESCRIPTION: SEQ ID NO: 29:

GAAACCTTGT TGAGTCCAAA ATGCGAACCC 30

( 2 ) INFORMATION FOR SEQ ID NO: 30:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) SEQUENCE DESCRIPTION: SEQ ID NO: 30:

TGTGCCCTTC TTTGCCAC 18

( 2 ) INFORMATION FOR SEQ ID NO: 31:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 31:

CAGTACTGGA TGTGGGTGAT GC 22

( 2 ) INFORMATION FOR SEQ ID NO: 32:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear (i i) SEQUENCE DESCRIPTION: SEQ ID NO: 32:

GTCATGCTAC TTTGGAATAT TTCTGGTGAT CCTTT                                           35

(2) INFORMATION FOR SEQ ID NO: 33:

(i) SEQUENCE CHARACTERISTICS:
        (A) LENGTH: 33
        (B) TYPE: nucleic acid
        (C) STRANDEDNESS: single
        (D) TOPOLOGY: linear (i i) SEQUENCE DESCRIPTION: SEQ ID NO: 33:

CAATACATGG ATGATTTGTA TGTAGGATCT GAC                                             33

(2) INFORMATION FOR SEQ ID NO: 34:

(i) SEQUENCE CHARACTERISTICS:
        (A) LENGTH: 28
        (B) TYPE: nucleic acid
        (C) STRANDEDNESS: single
        (D) TOPOLOGY: linear (i i) SEQUENCE DESCRIPTION: SEQ ID NO: 34:

ACCAAAGGAA TGGAGGTTCT TTCTGATG                                                   28

(2) INFORMATION FOR SEQ ID NO: 35:

(i) SEQUENCE CHARACTERISTICS:
        (A) LENGTH: 28
        (B) TYPE: nucleic acid
        (C) STRANDEDNESS: single
        (D) TOPOLOGY: linear (i i) SEQUENCE DESCRIPTION: SEQ ID NO: 35:

GCATTAGGAA TCATTCAAGC ACAACCAG                                                   28

(2) INFORMATION FOR SEQ ID NO: 36:

(i) SEQUENCE CHARACTERISTICS:
        (A) LENGTH: 34
        (B) TYPE: nucleic acid
        (C) STRANDEDNESS: single
        (D) TOPOLOGY: linear (i i) SEQUENCE DESCRIPTION: SEQ ID NO: 36:

GCACTGACTA ATTTATCTAC TTGTTCATTT CCTC                                            34

(2) INFORMATION FOR SEQ ID NO: 37:

(i) SEQUENCE CHARACTERISTICS:
        (A) LENGTH: 38
        (B) TYPE: nucleic acid
        (C) STRANDEDNESS: single
        (D) TOPOLOGY: linear (i i) SEQUENCE DESCRIPTION: SEQ ID NO: 37:

GGGATTGGAG GAAATGAACA AGTAGATAAA TTAGTCAG                                        38

(2) INFORMATION FOR SEQ ID NO: 38:

(i) SEQUENCE CHARACTERISTICS:
        (A) LENGTH: 35
        (B) TYPE: nucleic acid
        (C) STRANDEDNESS: single
        (D) TOPOLOGY: linear (i i) SEQUENCE DESCRIPTION: SEQ ID NO: 38:

TGTGTACAAT CTAGTTGCCA TATTCCTGGA CTACA   35

(2) INFORMATION FOR SEQ ID NO: 39:

(i) SEQUENCE CHARACTERISTICS:
        (A) LENGTH: 22
        (B) TYPE: nucleic acid
        (C) STRANDEDNESS: single
        (D) TOPOLOGY: linear (ii) SEQUENCE DESCRIPTION: SEQ ID NO: 39:

CAAATGGCAG TATTCATCCA CA   22

(2) INFORMATION FOR SEQ ID NO: 40:

(i) SEQUENCE CHARACTERISTICS:
        (A) LENGTH: 23
        (B) TYPE: nucleic acid
        (C) STRANDEDNESS: single
        (D) TOPOLOGY: linear (ii) SEQUENCE DESCRIPTION: SEQ ID NO: 40:

GTTTGTATGT CTGTTGCTAT TAT   23

(2) INFORMATION FOR SEQ ID NO: 41:

(i) SEQUENCE CHARACTERISTICS:
        (A) LENGTH: 18
        (B) TYPE: nucleic acid
        (C) STRANDEDNESS: single
        (D) TOPOLOGY: linear (ii) SEQUENCE DESCRIPTION: SEQ ID NO: 41:

CCCTTCACCT TTCCAGAG   18

(2) INFORMATION FOR SEQ ID NO: 42:

(i) SEQUENCE CHARACTERISTICS:
        (A) LENGTH: 27
        (B) TYPE: nucleic acid
        (C) STRANDEDNESS: single
        (D) TOPOLOGY: linear (ii) SEQUENCE DESCRIPTION: SEQ ID NO: 42:

GAGCCCTGGA AGCATCCAGG AAGTCAG   27

(2) INFORMATION FOR SEQ ID NO: 43:

(i) SEQUENCE CHARACTERISTICS:
        (A) LENGTH: 21
        (B) TYPE: nucleic acid
        (C) STRANDEDNESS: single
        (D) TOPOLOGY: linear (ii) SEQUENCE DESCRIPTION: SEQ ID NO: 43:

CTTCGTCGCT GTCTCCGCTT C   21

(2) INFORMATION FOR SEQ ID NO: 44:

(i) SEQUENCE CHARACTERISTICS:
        (A) LENGTH: 27
        (B) TYPE: nucleic acid
        (C) STRANDEDNESS: single
        (D) TOPOLOGY: linear (ii) SEQUENCE DESCRIPTION: SEQ ID NO: 44:

CAAGGGACTT TCCGCTGGGG ACTTTCC   27

( 2 ) INFORMATION FOR SEQ ID NO: 45:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( i i ) SEQUENCE DESCRIPTION: SEQ ID NO: 45:

GTCTAACCAG AGAGACCCAG TACAGGC 27

( 2 ) INFORMATION FOR SEQ ID NO: 46:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO: 46:

GTACTGGGTC TCTCTGGTTA GACCA 25

( 2 ) INFORMATION FOR SEQ ID NO: 47:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( i i ) SEQUENCE DESCRIPTION: SEQ ID NO: 47:

CACACAACAG ACGGGCACAC ACTACTTG 28

( 2 ) INFORMATION FOR SEQ ID NO: 48:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO: 48:

CTGAGGGATC TCTAGTTACC AGAGT 25

( 2 ) INFORMATION FOR SEQ ID NO: 49:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) SEQUENCE DESCRIPTION: SEQ ID NO: 49:

CTCTGGTAAC TAGAGATCCC TCA 23

( 2 ) INFORMATION FOR SEQ ID NO: 50:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) SEQUENCE DESCRIPTION: SEQ ID NO: 50:

GTTCGGGCGC CACTGCTAGA GAT 23

( 2 ) INFORMATION FOR SEQ ID NO: 51:

( i ) SEQUENCE CHARACTERISTICS:
    ( A ) LENGTH: 23
    ( B ) TYPE: nucleic acid
    ( C ) STRANDEDNESS: single
    ( D ) TOPOLOGY: linear ( i i ) SEQUENCE DESCRIPTION: SEQ ID NO: 51:

GCAAGCCGAGT CCTGCGTCG AGA 23

( 2 ) INFORMATION FOR SEQ ID NO: 52:

( i ) SEQUENCE CHARACTERISTICS:
    ( A ) LENGTH: 27
    ( B ) TYPE: nucleic acid
    ( C ) STRANDEDNESS: single
    ( D ) TOPOLOGY: linear ( i i ) SEQUENCE DESCRIPTION: SEQ ID NO: 52:

AATTTAATAC GACTCACTAT AGGGAGA 27

( 2 ) INFORMATION FOR SEQ ID NO: 53:

( i ) SEQUENCE CHARACTERISTICS:
    ( A ) LENGTH: 31
    ( B ) TYPE: nucleic acid
    ( C ) STRANDEDNESS: single
    ( D ) TOPOLOGY: linear ( i i ) SEQUENCE DESCRIPTION: SEQ ID NO: 53:

CCCATCTCTC TCCTTCTAGC CTCCGCTAGT C 31

( 2 ) INFORMATION FOR SEQ ID NO: 54:

( i ) SEQUENCE CHARACTERISTICS:
    ( A ) LENGTH: 31
    ( B ) TYPE: nucleic acid
    ( C ) STRANDEDNESS: single
    ( D ) TOPOLOGY: linear ( i i ) SEQUENCE DESCRIPTION: SEQ ID NO: 54:

CATGGGTATT ACTTCTGGGC TGAAAGCCTT C 31

( 2 ) INFORMATION FOR SEQ ID NO: 55:

( i ) SEQUENCE CHARACTERISTICS:
    ( A ) LENGTH: 30
    ( B ) TYPE: nucleic acid
    ( C ) STRANDEDNESS: single
    ( D ) TOPOLOGY: linear ( i i ) SEQUENCE DESCRIPTION: SEQ ID NO: 55:

AGTGGGGGA CATCAAGCAG CCATGCAAAT 30

( 2 ) INFORMATION FOR SEQ ID NO: 56:

( i ) SEQUENCE CHARACTERISTICS:
    ( A ) LENGTH: 26
    ( B ) TYPE: nucleic acid
    ( C ) STRANDEDNESS: single
    ( D ) TOPOLOGY: linear ( i i ) SEQUENCE DESCRIPTION: SEQ ID NO: 56:

GGCCAGATGA GAGAACCAAG GGGAAG 26

( 2 ) INFORMATION FOR SEQ ID NO: 57:

( i ) SEQUENCE CHARACTERISTICS:

(A) LENGTH: 37
            (B) TYPE: nucleic acid
            (C) STRANDEDNESS: single
            (D) TOPOLOGY: linear (i i) SEQUENCE DESCRIPTION: SEQ ID NO: 57:

CTACTAGTAC CCTTCAGGAA CAAATAGGAT GGATGAC                                37

(2) INFORMATION FOR SEQ ID NO: 58:

(i) SEQUENCE CHARACTERISTICS:
            (A) LENGTH: 33
            (B) TYPE: nucleic acid
            (C) STRANDEDNESS: single
            (D) TOPOLOGY: linear (i i) SEQUENCE DESCRIPTION: SEQ ID NO: 58:

CACTAGAAGA AATGATGACA GCATGTCAGG GAG                                    33

(2) INFORMATION FOR SEQ ID NO: 59:

(i) SEQUENCE CHARACTERISTICS:
            (A) LENGTH: 31
            (B) TYPE: nucleic acid
            (C) STRANDEDNESS: single
            (D) TOPOLOGY: linear (i i) SEQUENCE DESCRIPTION: SEQ ID NO: 59:

GGGATTAGAT ATCAGTACAA TGTGCTTCCA C                                      31

(2) INFORMATION FOR SEQ ID NO: 60:

(i) SEQUENCE CHARACTERISTICS:
            (A) LENGTH: 37
            (B) TYPE: nucleic acid
            (C) STRANDEDNESS: single
            (D) TOPOLOGY: linear (i i) SEQUENCE DESCRIPTION: SEQ ID NO: 60:

TTAGAAATAG GGCAGCATAG AACAAAAATA GAGGAGC                                37

(2) INFORMATION FOR SEQ ID NO: 61:

(i) SEQUENCE CHARACTERISTICS:
            (A) LENGTH: 23
            (B) TYPE: nucleic acid
            (C) STRANDEDNESS: single
            (D) TOPOLOGY: linear (i i) SEQUENCE DESCRIPTION: SEQ ID NO: 61:

GCATGGGTAC CAGCACACAA AGG                                               23

(2) INFORMATION FOR SEQ ID NO: 62:

(i) SEQUENCE CHARACTERISTICS:
            (A) LENGTH: 29
            (B) TYPE: nucleic acid
            (C) STRANDEDNESS: single
            (D) TOPOLOGY: linear (i i) SEQUENCE DESCRIPTION: SEQ ID NO: 62:

GGGGTACAGT GCAGGGGAAA GAATAGTAG                                         29

(2) INFORMATION FOR SEQ ID NO: 63:

(i) SEQUENCE CHARACTERISTICS:
            (A) LENGTH: 29
            (B) TYPE: nucleic acid ( C ) STRANDEDNESS: single
( D ) TOPOLOGY: linear ( i i ) SEQUENCE DESCRIPTION: SEQ ID NO: 63:

TTCCTGCCAT AGGAGATGCC TAAGGCTTT                29

( 2 ) INFORMATION FOR SEQ ID NO: 64:

( i ) SEQUENCE CHARACTERISTICS:
    ( A ) LENGTH: 28
    ( B ) TYPE: nucleic acid
    ( C ) STRANDEDNESS: single
    ( D ) TOPOLOGY: linear ( i i ) SEQUENCE DESCRIPTION: SEQ ID NO: 64:

CCCTCAGATC CTGCATATAA GCAGCTGC                 28

( 2 ) INFORMATION FOR SEQ ID NO: 65:

( i ) SEQUENCE CHARACTERISTICS:
    ( A ) LENGTH: 33
    ( B ) TYPE: nucleic acid
    ( C ) STRANDEDNESS: single
    ( D ) TOPOLOGY: linear ( i i ) SEQUENCE DESCRIPTION: SEQ ID NO: 65:

CCCACTGCTT AAGCCTCAAT AAAGCTTGCC TTG           33

( 2 ) INFORMATION FOR SEQ ID NO: 66:

( i ) SEQUENCE CHARACTERISTICS:
    ( A ) LENGTH: 28
    ( B ) TYPE: nucleic acid
    ( C ) STRANDEDNESS: single
    ( D ) TOPOLOGY: linear ( i i ) SEQUENCE DESCRIPTION: SEQ ID NO: 66:

TCCCTGTTCG GGCGCCACTG CTAGAGAT                 28

( 2 ) INFORMATION FOR SEQ ID NO: 67:

( i ) SEQUENCE CHARACTERISTICS:
    ( A ) LENGTH: 31
    ( B ) TYPE: nucleic acid
    ( C ) STRANDEDNESS: single
    ( D ) TOPOLOGY: linear ( i i ) SEQUENCE DESCRIPTION: SEQ ID NO: 67:

GACUAGCGGA GGCUAGAAGG AGAGAGAUGG G             31

( 2 ) INFORMATION FOR SEQ ID NO: 68:

( i ) SEQUENCE CHARACTERISTICS:
    ( A ) LENGTH: 31
    ( B ) TYPE: nucleic acid
    ( C ) STRANDEDNESS: single
    ( D ) TOPOLOGY: linear ( i i ) SEQUENCE DESCRIPTION: SEQ ID NO: 68:

GAAGGCUUUC AGCCCAGAAG UAAUACCCAU G             31

( 2 ) INFORMATION FOR SEQ ID NO: 69:

( i ) SEQUENCE CHARACTERISTICS:
    ( A ) LENGTH: 30
    ( B ) TYPE: nucleic acid
    ( C ) STRANDEDNESS: single
    ( D ) TOPOLOGY: linear (i i) SEQUENCE DESCRIPTION: SEQ ID NO: 69:

AUUUGCAUGG CUGCUUGAUG UCCCCCCACU     30

(2) INFORMATION FOR SEQ ID NO: 70:

(i) SEQUENCE CHARACTERISTICS:
        (A) LENGTH: 26
        (B) TYPE: nucleic acid
        (C) STRANDEDNESS: single
        (D) TOPOLOGY: linear (i i) SEQUENCE DESCRIPTION: SEQ ID NO: 70:

CUUCCCCUUG GUUCUCUCAU CUGGCC     26

(2) INFORMATION FOR SEQ ID NO: 71:

(i) SEQUENCE CHARACTERISTICS:
        (A) LENGTH: 37
        (B) TYPE: nucleic acid
        (C) STRANDEDNESS: single
        (D) TOPOLOGY: linear (i i) SEQUENCE DESCRIPTION: SEQ ID NO: 71:

GUCAUCCAUC CUAUUUGUUC CUGAAGGGUA CUAGUAG     37

(2) INFORMATION FOR SEQ ID NO: 72:

(i) SEQUENCE CHARACTERISTICS:
        (A) LENGTH: 33
        (B) TYPE: nucleic acid
        (C) STRANDEDNESS: single
        (D) TOPOLOGY: linear (i i) SEQUENCE DESCRIPTION: SEQ ID NO: 72:

CUCCCUGACA UGCUGUCAUC AUUUCUUCUA GUG     33

(2) INFORMATION FOR SEQ ID NO: 73:

(i) SEQUENCE CHARACTERISTICS:
        (A) LENGTH: 31
        (B) TYPE: nucleic acid
        (C) STRANDEDNESS: single
        (D) TOPOLOGY: linear (i i) SEQUENCE DESCRIPTION: SEQ ID NO: 73:

GUGGAAGCAC AUUGUACUGA UAUCUAAUCC C     31

(2) INFORMATION FOR SEQ ID NO: 74:

(i) SEQUENCE CHARACTERISTICS:
        (A) LENGTH: 37
        (B) TYPE: nucleic acid
        (C) STRANDEDNESS: single
        (D) TOPOLOGY: linear (i i) SEQUENCE DESCRIPTION: SEQ ID NO: 74:

GCUCCUCUAU UUUUGUUCUA UGCUGCCCUA UUUCUAA     37

(2) INFORMATION FOR SEQ ID NO: 75:

(i) SEQUENCE CHARACTERISTICS:
        (A) LENGTH: 23
        (B) TYPE: nucleic acid
        (C) STRANDEDNESS: single
        (D) TOPOLOGY: linear (i i) SEQUENCE DESCRIPTION: SEQ ID NO: 75:

```
CCUUUGUGUG CUGGUACCCA UGC                                                    23
```

(2) INFORMATION FOR SEQ ID NO: 76:

(i) SEQUENCE CHARACTERISTICS:
        (A) LENGTH: 29
        (B) TYPE: nucleic acid
        (C) STRANDEDNESS: single
        (D) TOPOLOGY: linear (ii) SEQUENCE DESCRIPTION: SEQ ID NO: 76:

```
CUACUAUUCU UUCCCCUGCA CUGUACCCC                                              29
```

(2) INFORMATION FOR SEQ ID NO: 77:

(i) SEQUENCE CHARACTERISTICS:
        (A) LENGTH: 29
        (B) TYPE: nucleic acid
        (C) STRANDEDNESS: single
        (D) TOPOLOGY: linear (ii) SEQUENCE DESCRIPTION: SEQ ID NO: 77:

```
AAAGCCUUAG GCAUCUCCUA UGGCAGGAA                                              29
```

(2) INFORMATION FOR SEQ ID NO: 78:

(i) SEQUENCE CHARACTERISTICS:
        (A) LENGTH: 28
        (B) TYPE: nucleic acid
        (C) STRANDEDNESS: single
        (D) TOPOLOGY: linear (ii) SEQUENCE DESCRIPTION: SEQ ID NO: 78:

```
GCAGCUGCUU AUAUGCAGGA UCUGAGGG                                               28
```

(2) INFORMATION FOR SEQ ID NO: 79:

(i) SEQUENCE CHARACTERISTICS:
        (A) LENGTH: 33
        (B) TYPE: nucleic acid
        (C) STRANDEDNESS: single
        (D) TOPOLOGY: linear (ii) SEQUENCE DESCRIPTION: SEQ ID NO: 79:

```
CAAGGCAAGC UUUAUUGAGG CUUAAGCAGU GGG                                         33
```

(2) INFORMATION FOR SEQ ID NO: 80:

(i) SEQUENCE CHARACTERISTICS:
        (A) LENGTH: 28
        (B) TYPE: nucleic acid
        (C) STRANDEDNESS: single
        (D) TOPOLOGY: linear (ii) SEQUENCE DESCRIPTION: SEQ ID NO: 80:

```
AUCUCUAGCA GUGGCGCCCG AACAGGGA                                               28
```

(2) INFORMATION FOR SEQ ID NO: 81:

(i) SEQUENCE CHARACTERISTICS:
        (A) LENGTH: 31
        (B) TYPE: nucleic acid
        (C) STRANDEDNESS: single
        (D) TOPOLOGY: linear (ii) SEQUENCE DESCRIPTION: SEQ ID NO: 81:

```
CCCAUCUCUC UCCUUCUAGC CUCCGCUAGU C                                           31
```

( 2 ) INFORMATION FOR SEQ ID NO: 82:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( i i ) SEQUENCE DESCRIPTION: SEQ ID NO: 82:

CAUGGGUAUU ACUUCUGGGC UGAAAGCCUU C        31

( 2 ) INFORMATION FOR SEQ ID NO: 83:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) SEQUENCE DESCRIPTION: SEQ ID NO: 83:

AGUGGGGGA CAUCAAGCAG CCAUGCAAAU        30

( 2 ) INFORMATION FOR SEQ ID NO: 84:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO: 84:

GGCCAGAUGA GAGAACCAAG GGGAAG        26

( 2 ) INFORMATION FOR SEQ ID NO: 85:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( i i ) SEQUENCE DESCRIPTION: SEQ ID NO: 85:

CUACUAGUAC CCUUCAGGAA CAAAUAGGAU GGAUGAC        37

( 2 ) INFORMATION FOR SEQ ID NO: 86:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( i i ) SEQUENCE DESCRIPTION: SEQ ID NO: 86:

CACUAGAAGA AAUGAUGACA GCAUGUCAGG GAG        33

( 2 ) INFORMATION FOR SEQ ID NO: 87:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( i i ) SEQUENCE DESCRIPTION: SEQ ID NO: 87:

GGGAUUAGAU AUCAGUACAA UGUGCUUCCA C        31

( 2 ) INFORMATION FOR SEQ ID NO: 88:

( i ) SEQUENCE CHARACTERISTICS:
    ( A ) LENGTH: 37
    ( B ) TYPE: nucleic acid
    ( C ) STRANDEDNESS: single
    ( D ) TOPOLOGY: linear ( i i ) SEQUENCE DESCRIPTION: SEQ ID NO: 88:

UUAGAAAUAG GGCAGCAUAG AACAAAAAUA GAGGAGC    37

( 2 ) INFORMATION FOR SEQ ID NO: 89:

( i ) SEQUENCE CHARACTERISTICS:
    ( A ) LENGTH: 23
    ( B ) TYPE: nucleic acid
    ( C ) STRANDEDNESS: single
    ( D ) TOPOLOGY: linear ( i i ) SEQUENCE DESCRIPTION: SEQ ID NO: 89:

GCAUGGGUAC CAGCACACAA AGG    23

( 2 ) INFORMATION FOR SEQ ID NO: 90:

( i ) SEQUENCE CHARACTERISTICS:
    ( A ) LENGTH: 29
    ( B ) TYPE: nucleic acid
    ( C ) STRANDEDNESS: single
    ( D ) TOPOLOGY: linear ( i i ) SEQUENCE DESCRIPTION: SEQ ID NO: 90:

GGGGUACAGU GCAGGGGAAA GAAUAGUAG    29

( 2 ) INFORMATION FOR SEQ ID NO: 91:

( i ) SEQUENCE CHARACTERISTICS:
    ( A ) LENGTH: 29
    ( B ) TYPE: nucleic acid
    ( C ) STRANDEDNESS: single
    ( D ) TOPOLOGY: linear ( i i ) SEQUENCE DESCRIPTION: SEQ ID NO: 91:

UUCCUGCCAU AGGAGAUGCC UAAGGCUUU    29

( 2 ) INFORMATION FOR SEQ ID NO: 92:

( i ) SEQUENCE CHARACTERISTICS:
    ( A ) LENGTH: 28
    ( B ) TYPE: nucleic acid
    ( C ) STRANDEDNESS: single
    ( D ) TOPOLOGY: linear ( i i ) SEQUENCE DESCRIPTION: SEQ ID NO: 92:

CCCUCAGAUC CUGCAUAUAA GCAGCUGC    28

( 2 ) INFORMATION FOR SEQ ID NO: 93:

( i ) SEQUENCE CHARACTERISTICS:
    ( A ) LENGTH: 33
    ( B ) TYPE: nucleic acid
    ( C ) STRANDEDNESS: single
    ( D ) TOPOLOGY: linear ( i i ) SEQUENCE DESCRIPTION: SEQ ID NO: 93:

CCCACUGCUU AAGCCUCAAU AAAGCUUGCC UUG    33

( 2 ) INFORMATION FOR SEQ ID NO: 94:

( i ) SEQUENCE CHARACTERISTICS:
    ( A ) LENGTH: 28
    ( B ) TYPE: nucleic acid
    ( C ) STRANDEDNESS: single
    ( D ) TOPOLOGY: linear ( i i ) SEQUENCE DESCRIPTION: SEQ ID NO: 94:

UCCCUGUUCG GGCGCCACUG CUAGAGAU    28

( 2 ) INFORMATION FOR SEQ ID NO: 95:

( i ) SEQUENCE CHARACTERISTICS:
    ( A ) LENGTH: 24
    ( B ) TYPE: nucleic acid
    ( C ) STRANDEDNESS: single
    ( D ) TOPOLOGY: linear ( i i ) SEQUENCE DESCRIPTION: SEQ ID NO: 95:

CCGCTTAATA CTGACGCTCT CGCA    24

( 2 ) INFORMATION FOR SEQ ID NO: 96:

( i ) SEQUENCE CHARACTERISTICS:
    ( A ) LENGTH: 36
    ( B ) TYPE: nucleic acid
    ( C ) STRANDEDNESS: single
    ( D ) TOPOLOGY: linear ( i i ) SEQUENCE DESCRIPTION: SEQ ID NO: 96:

GGGATGGAAA GGATCACCAG CAATATTCCA AAGTAG    36

( 2 ) INFORMATION FOR SEQ ID NO: 97:

( i ) SEQUENCE CHARACTERISTICS:
    ( A ) LENGTH: 33
    ( B ) TYPE: nucleic acid
    ( C ) STRANDEDNESS: single
    ( D ) TOPOLOGY: linear ( i i ) SEQUENCE DESCRIPTION: SEQ ID NO: 97:

CATCCACAAT TTTAAAAGAA AAGGGGGAT TGG    33

( 2 ) INFORMATION FOR SEQ ID NO: 98:

( i ) SEQUENCE CHARACTERISTICS:
    ( A ) LENGTH: 24
    ( B ) TYPE: nucleic acid
    ( C ) STRANDEDNESS: single
    ( D ) TOPOLOGY: linear ( i i ) SEQUENCE DESCRIPTION: SEQ ID NO: 98:

TGGGCGGGAC TGGGGAGTGG CGAG    24

( 2 ) INFORMATION FOR SEQ ID NO: 99:

( i ) SEQUENCE CHARACTERISTICS:
    ( A ) LENGTH: 24
    ( B ) TYPE: nucleic acid
    ( C ) STRANDEDNESS: single
    ( D ) TOPOLOGY: linear ( i i ) SEQUENCE DESCRIPTION: SEQ ID NO: 99:

CUCGACGCAG GACUCGGCUU GCUG    24

( 2 ) INFORMATION FOR SEQ ID NO: 100:

( i ) SEQUENCE CHARACTERISTICS:
    ( A ) LENGTH: 23

( B ) TYPE: nucleic acid
        ( C ) STRANDEDNESS: single
        ( D ) TOPOLOGY: linear ( i i ) SEQUENCE DESCRIPTION: SEQ ID NO: 100:

CUCCCCCGCU UAAUACUGAC GCU     23

( 2 ) INFORMATION FOR SEQ ID NO: 101:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( i i ) SEQUENCE DESCRIPTION: SEQ ID NO: 101:

GGCAAAUGGU ACAUCAGGCC AUAUCACCUA G     31

( 2 ) INFORMATION FOR SEQ ID NO: 102:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO: 102:

GGGGUGGCUC CUUCUGAUAA UGCUG     25

( 2 ) INFORMATION FOR SEQ ID NO: 103:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO: 103:

CAGAAGGAGC CACCCCACAA GAUUUA     26

( 2 ) INFORMATION FOR SEQ ID NO: 104:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( i i ) SEQUENCE DESCRIPTION: SEQ ID NO: 104:

GACCAUCAAU GAGGAAGCUG CAGAAUG     27

( 2 ) INFORMATION FOR SEQ ID NO: 105:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO: 105:

CCCAUUCUGC AGCUUCCUCA UUGAU     25

( 2 ) INFORMATION FOR SEQ ID NO: 106:

( i ) SEQUENCE CHARACTERISTICS:
        ( A ) LENGTH: 19
        ( B ) TYPE: nucleic acid
        ( C ) STRANDEDNESS: single ( D ) TOPOLOGY: linear ( i i ) SEQUENCE DESCRIPTION: SEQ ID NO: 106:

AGUGACAUAG CAGGAACUA 19

( 2 ) INFORMATION FOR SEQ ID NO: 107:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO: 107:

CCAUCCUAUU UGUUCCUGAA GGGUAC 26

( 2 ) INFORMATION FOR SEQ ID NO: 108:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) SEQUENCE DESCRIPTION: SEQ ID NO: 108:

AGAUUUCUCC UACUGGGAUA GGU 23

( 2 ) INFORMATION FOR SEQ ID NO: 109:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) SEQUENCE DESCRIPTION: SEQ ID NO: 109:

GAAACCUUGU UGAGUCCAAA AUGCGAACCC 30

( 2 ) INFORMATION FOR SEQ ID NO: 110:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) SEQUENCE DESCRIPTION: SEQ ID NO: 110:

UGUGCCCUUC UUUGCCAC 18

( 2 ) INFORMATION FOR SEQ ID NO: 111:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 111:

CAGUACUGGA UGUGGGUGAU GC 22

( 2 ) INFORMATION FOR SEQ ID NO: 112:

( i ) SEQUENCE CHARACTERISTICS:
        ( A ) LENGTH: 35
        ( B ) TYPE: nucleic acid
        ( C ) STRANDEDNESS: single
        ( D ) TOPOLOGY: linear (i i) SEQUENCE DESCRIPTION: SEQ ID NO: 112:

GUCAUGCUAC UUUGGAAUAU UUCUGGUGAU CCUUU     35

(2) INFORMATION FOR SEQ ID NO: 113:

(i) SEQUENCE CHARACTERISTICS:
        (A) LENGTH: 33
        (B) TYPE: nucleic acid
        (C) STRANDEDNESS: single
        (D) TOPOLOGY: linear (i i) SEQUENCE DESCRIPTION: SEQ ID NO: 113:

CAAUACAUGG AUGAUUUGUA UGUAGGAUCU GAC     33

(2) INFORMATION FOR SEQ ID NO: 114:

(i) SEQUENCE CHARACTERISTICS:
        (A) LENGTH: 28
        (B) TYPE: nucleic acid
        (C) STRANDEDNESS: single
        (D) TOPOLOGY: linear (i i) SEQUENCE DESCRIPTION: SEQ ID NO: 114:

ACCAAAGGAA UGGAGGUUCU UUCUGAUG     28

(2) INFORMATION FOR SEQ ID NO: 115:

(i) SEQUENCE CHARACTERISTICS:
        (A) LENGTH: 28
        (B) TYPE: nucleic acid
        (C) STRANDEDNESS: single
        (D) TOPOLOGY: linear (i i) SEQUENCE DESCRIPTION: SEQ ID NO: 115:

GCAUUAGGAA UCAUUCAAGC ACAACCAG     28

(2) INFORMATION FOR SEQ ID NO: 116:

(i) SEQUENCE CHARACTERISTICS:
        (A) LENGTH: 34
        (B) TYPE: nucleic acid
        (C) STRANDEDNESS: single
        (D) TOPOLOGY: linear (i i) SEQUENCE DESCRIPTION: SEQ ID NO: 116:

GCACUGACUA AUUUAUCUAC UUGUUCAUUU CCUC     34

(2) INFORMATION FOR SEQ ID NO: 117:

(i) SEQUENCE CHARACTERISTICS:
        (A) LENGTH: 38
        (B) TYPE: nucleic acid
        (C) STRANDEDNESS: single
        (D) TOPOLOGY: linear (i i) SEQUENCE DESCRIPTION: SEQ ID NO: 117:

GGGAUUGGAG GAAAUGAACA AGUAGAUAAA UUAGUCAG     38

(2) INFORMATION FOR SEQ ID NO: 118:

(i) SEQUENCE CHARACTERISTICS:
        (A) LENGTH: 35
        (B) TYPE: nucleic acid
        (C) STRANDEDNESS: single
        (D) TOPOLOGY: linear (i i) SEQUENCE DESCRIPTION: SEQ ID NO: 118:

UGUGUACAAU CUAGUUGCCA UAUUCCUGGA CUACA 35

( 2 ) INFORMATION FOR SEQ ID NO: 119:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 119:

CAAAUGGCAG UAUUCAUCCA CA 22

( 2 ) INFORMATION FOR SEQ ID NO: 120:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) SEQUENCE DESCRIPTION: SEQ ID NO: 120:

GUUUGUAUGU CUGUUGCUAU UAU 23

( 2 ) INFORMATION FOR SEQ ID NO: 121:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) SEQUENCE DESCRIPTION: SEQ ID NO: 121:

CCCUUCACCU UUCCAGAG 18

( 2 ) INFORMATION FOR SEQ ID NO: 122:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( i i ) SEQUENCE DESCRIPTION: SEQ ID NO: 122:

GAGCCCUGGA AGCAUCCAGG AAGUCAG 27

( 2 ) INFORMATION FOR SEQ ID NO: 123:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) SEQUENCE DESCRIPTION: SEQ ID NO: 123:

CUUCGUCGCU GUCUCCGCUU C 21

( 2 ) INFORMATION FOR SEQ ID NO: 124:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( i i ) SEQUENCE DESCRIPTION: SEQ ID NO: 124:

CAAGGGACUU UCCGCUGGGG ACUUCC 27

( 2 ) INFORMATION FOR SEQ ID NO: 125:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( i i ) SEQUENCE DESCRIPTION: SEQ ID NO: 125:

GUCUAACCAG AGAGACCCAG UACAGGC      27

( 2 ) INFORMATION FOR SEQ ID NO: 126:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO: 126:

GUACUGGGUC UCUCUGGUUA GACCA      25

( 2 ) INFORMATION FOR SEQ ID NO: 127:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( i i ) SEQUENCE DESCRIPTION: SEQ ID NO: 127:

CACACAACAG ACGGGCACAC ACUACUUG      28

( 2 ) INFORMATION FOR SEQ ID NO: 128:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO: 128:

CUGAGGGAUC UCUAGUUACC AGAGU      25

( 2 ) INFORMATION FOR SEQ ID NO: 129:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) SEQUENCE DESCRIPTION: SEQ ID NO: 129:

CUCUGGUAAC UAGAGAUCCC UCA      23

( 2 ) INFORMATION FOR SEQ ID NO: 130:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) SEQUENCE DESCRIPTION: SEQ ID NO: 130:

GUUCGGGCGC CACUGCUAGA GAU      23

( 2 ) INFORMATION FOR SEQ ID NO: 131:

( i ) SEQUENCE CHARACTERISTICS:
  ( A ) LENGTH: 23
  ( B ) TYPE: nucleic acid
  ( C ) STRANDEDNESS: single
  ( D ) TOPOLOGY: linear ( i i ) SEQUENCE DESCRIPTION: SEQ ID NO: 131:

GCAAGCCGAG UCCUGCGUCG AGA  23

( 2 ) INFORMATION FOR SEQ ID NO: 132:

( i ) SEQUENCE CHARACTERISTICS:
  ( A ) LENGTH: 24
  ( B ) TYPE: nucleic acid
  ( C ) STRANDEDNESS: single
  ( D ) TOPOLOGY: linear ( i i ) SEQUENCE DESCRIPTION: SEQ ID NO: 132:

UGCGAGAGCG UCAGUAUUAA GCGG  24

( 2 ) INFORMATION FOR SEQ ID NO: 133:

( i ) SEQUENCE CHARACTERISTICS:
  ( A ) LENGTH: 36
  ( B ) TYPE: nucleic acid
  ( C ) STRANDEDNESS: single
  ( D ) TOPOLOGY: linear ( i i ) SEQUENCE DESCRIPTION: SEQ ID NO: 133:

CUACUUUGGA AUAUUGCUGG UGAUCCUUUC CAUCCC  36

( 2 ) INFORMATION FOR SEQ ID NO: 134:

( i ) SEQUENCE CHARACTERISTICS:
  ( A ) LENGTH: 33
  ( B ) TYPE: nucleic acid
  ( C ) STRANDEDNESS: single
  ( D ) TOPOLOGY: linear ( i i ) SEQUENCE DESCRIPTION: SEQ ID NO: 134:

CCAAUCCCCC CUUUUCUUUU AAAAUUGUGG AUG  33

( 2 ) INFORMATION FOR SEQ ID NO: 135:

( i ) SEQUENCE CHARACTERISTICS:
  ( A ) LENGTH: 24
  ( B ) TYPE: nucleic acid
  ( C ) STRANDEDNESS: single
  ( D ) TOPOLOGY: linear ( i i ) SEQUENCE DESCRIPTION: SEQ ID NO: 135:

CUCGCCACUC CCCAGUCCCG CCCA  24

( 2 ) INFORMATION FOR SEQ ID NO: 136:

( i ) SEQUENCE CHARACTERISTICS:
  ( A ) LENGTH: 24
  ( B ) TYPE: nucleic acid
  ( C ) STRANDEDNESS: single
  ( D ) TOPOLOGY: linear ( i i ) SEQUENCE DESCRIPTION: SEQ ID NO: 136:

CCGCUUAAUA CUGACGCUCU CGCA  24

( 2 ) INFORMATION FOR SEQ ID NO: 137:

( i ) SEQUENCE CHARACTERISTICS:

-continued (A) LENGTH: 36
(B) TYPE: nucleic acid
(C) STRANDEDNESS: single
(D) TOPOLOGY: linear (i i) SEQUENCE DESCRIPTION: SEQ ID NO: 137:

GGGAUGGAAA GGAUCACCAG CAAUAUUCCA AAGUAG   36

(2) INFORMATION FOR SEQ ID NO: 138:

(i) SEQUENCE CHARACTERISTICS:
(A) LENGTH: 33
(B) TYPE: nucleic acid
(C) STRANDEDNESS: single
(D) TOPOLOGY: linear (i i) SEQUENCE DESCRIPTION: SEQ ID NO: 138:

CAUCCACAAU UUUAAAAGAA AAGGGGGAU UGG   33

(2) INFORMATION FOR SEQ ID NO: 139:

(i) SEQUENCE CHARACTERISTICS:
(A) LENGTH: 24
(B) TYPE: nucleic acid
(C) STRANDEDNESS: single
(D) TOPOLOGY: linear (i i) SEQUENCE DESCRIPTION: SEQ ID NO: 139:

UGGGCGGGAC UGGGGAGUGG CGAG   24

DETECTION OF HUMAN IMMUNODEFICIENCY VIRUS TYPE 1

This application is a continuation of McDonough et al., U.S. application Ser. No. 08/040,745, filed Mar. 26, 1993, now abandoned, the whole of which is hereby incorporated by reference herein; said Ser. No. 08/040,745, a continuation-in-part of Kacian and Fultz, entitled Nucleic Acid Sequence Amplification Methods, U.S. Ser. No. 07/379,501, filed Jul. 11, 1989, now abandoned, and a continuation-in-part of Kacian and Fultz, entitled "Nucleic Acid Sequence Amplification Methods," U.S. Ser. No. 07/550,837, filed Jul. 10, 1990, now U.S. Pat. No. 5,480,784, both hereby incorporated by reference herein.

FIELD OF THE INVENTION

This invention relates to the design and construction of amplification oligonucleotides and probes to Human Immunodeficiency Virus Type 1 (HIV), which allow detection of the organism in a test sample.

BACKGROUND OF THE INVENTION

This section provides a brief outline of relevant areas. None of the art cited or referred to is admitted to be prior art to the claims. Laboratory diagnosis of Human Immunodeficiency Virus Type 1 in humans is currently performed by demonstration of the presence of viral antigen (p24) or anti-HIV-1 antibodies in serum. Direct detection of viral DNA, however, is a more useful diagnostic tool in some populations, such as infants born to seropositive mothers. Detection of viral DNA is more rapid and less hazardous than culture. Direct hybridization lacks adequate sensitivity in most patients (Shaw et al. *Science* 226:1165–1171, 1984). Many references mention oligonucleotides said to have use in detection of Human Immunodeficiency Virus. Most of these references also mention the use of polymerase chain reaction (PCR). These references include the following: Kwok et al., *J. Virol.* 61: 1690–1694, 1987; Agius et al., *J. Virol. Meth.*, 30:141– 150, 1990; Albert and Fenyo, *J. Clin. Microbiol.* 28:1560–1564, 1990; Bell and Ratner, *AIDS Res. and Human Retroviruses* 5:87–95, 1989; Bruisten et al., *Vox Sang* 61:24–29, 1991; Clarke et al., *AIDS* 4:1133–1136, 1990; Coutlee et al., *Anal. Biochem.* 181:96–105, 1989; Dahlen et al., *J. Clin. Microbiol.* 29:798–804, 1991; Dudding et al., *Biochem. Biophys. Res. Comm.* 167:244–250, 1990; Ferrer-Le-Coeur et al., *Thrombosis and Haemostasis* 65:478–482, 1991; Goswami et al., *AIDS* 5:797–803, 1991; Grankvist et al., *AIDS* 5:575–578, 1991; Guatelli et al., *J. Virol.* 64:4093–4098, 1990; Hart et al., *Lancet* 2 (8611):596–599, 1988; Holland et al., *Proc. Natl. Acad. Sci. USA,* 88:7276–7280, 1991; Keller et al., *Anal. Biochem.* 177:27–32, 1989; Kumar et al., *AIDS Res. and Human Retroviruses* 5:345–354, 1989; Linz et al., *J. Clin. Chem. Clin. Biochem.* 28:5–13, 1990; Mano and Chermann, *Res. Virol.* 142:95–104, 1991; Mariotti et al., *AIDS* 4:633–637, 1990; Mariotti et al., *Transfusion* 30:704–706, 1990; Meyerhans et al., *Cell* 58:901–910, 1989; Mousset et al., *AIDS* 4:1225–1230, 1990; Ou et al., *Science* 239:295–297, 1988; Pang et al., *Nature* 343:85–89, 1990; Paterlini et al., *J. Med. Virol.* 30:53–57, 1990; Perrin et al., *Blood* 76:641–645, 1990; Preston et al., *J. Virol. Meth.* 33:383–390, 1991; Pritchard and Stefano, *Ann. Biol. Clin.* 48:492–497, 1990; Rudin et al., *Eur. J. Clin. Microbiol. Infect. Dis.* 10:146–156, 1991; Shoebridge et al., *AIDS* 5:221–224, 1991; Stevenson et al., *J. Virol.* 64:3792–3803, 1990; Truckenmiller et al., *Res. Immunol.* 140:527–544, 1989; Van de Perre, et al., *New Eng. J. Med.* 325:593–598, 1991; Varas et al., *BioTechniques* 11:384–391, 1991; Velpandi et al., *J. Virol.* 65:4847–4852, 1991; Williams et al., *AIDS* 4:393–398, 1990; Zachar et al., *J. Virol. Meth.* 33:391–395, 1991; Zack et al. *Cell* 61:213–222, 1990; Findlay et al., entitled "Nucleic acid test article and its use to detect a predetermined nucleic acid," PCT/US90/00452; Publication No. WO 90/08040 Gingeras et al., entitled "Nucleic acid probe assay methods and compositions," PCT/US87/01966; Publication No. WO 88/01302 Brakel and Spadoro, entitled "Amplification capture assay," EPO application number 90124738.7, publication number 0 435 150 A2; Moncany and Montagnier, entitled "Séquences nucléotidiques issues du génome des rétrovirus du typ hiv-1, hiv-2 et siv, et leurs applications notamment pour l'amplification des génomes de ces retrovirus et pour le diagnostic in-vitro des infections dues á ces virus," EPO application number 90401520.3, publication number 0 403 333 A2; Urdea, entitled "DNA-dependent RNA polymerase transcripts as reporter molecules for signal amplification in nucleic acid hybridization assays," PCT/US91/00213; Musso et al., entitled "Lanthanide chelate-tagged nucleic acid probes," PCT/US88/03735; Publication No. WO 89/04375 Chang, entitled "Cloning and expression of HTLV-III DNA," EPO application number 85307260.1, publication number 0 185 444 A2; and Levenson, entitled "Diagnostic kit and method using a solid phase capture means for detecting nucleic acids," EPO application number 89311862.0, publication number 0 370 694; and Sninsky et al., U.S. Pat. No. 5,008,182.

SUMMARY OF THE INVENTION

This invention discloses novel amplification oligonucleotides and detection probes for the detection of Human Immunodeficiency Virus Type 1. The probes are capable of distinguishing between the Human Immunodeficiency Virus type 1 and its known closest phylogenetic neighbors. The amplification oligonucleotides and probes may be used in an assay for the detection and/or quantitation of Human Immunodeficiency Virus nucleic acid.

It is known that a nucleic acid sequence able to hybridize to a nucleic acid sequence sought to be detected ("target sequence") can serve as a probe for the target sequence. The probe may be labelled with a detectable moiety such as a radioisotope, antigen or chemiluminescent moiety to facilitate detection of the target sequence. A background description of the use of nucleic acid hybridization as a procedure for the detection of particular nucleic-acid sequences is provided in Kohne, U.S. Pat. No. 4,851,330, and Hogan et al., EPO Patent Application No. PCT/US87/03009, entitled "Nucleic Acid Probes for Detection and/or Quantitation of Non-Viral Organisms."

It is also known that hybridization may occur between complementary nucleic acid strands including; DNA/DNA, DNA/RNA, and RNA/RNA. Two single strands of deoxyribo-("DNA") or ribo-("RNA") nucleic acid, formed from nucleotides (including the bases adenine (A), cytosine (C), thymidine (T), guanine (G), uracil (U), or inosine (I)), may hybridize to form a double-stranded structure in which the two strands are held together by hydrogen bonds between pairs of complementary bases. Generally, A is hydrogen bonded to T or U, while G is hydrogen bonded to C. At any point along the hybridized strands, therefore, one may find the classical base pairs AT or AU, TA or UA, GC, or CG. Thus, when a first single strand of nucleic acid contains sufficient contiguous complementary bases to a second, and those two strands are brought together under conditions which will promote their hybridization, double-stranded nucleic acid will result. Under appropriate conditions, DNA/DNA, RNA/DNA, or RNA/RNA hybrids may be formed. The present invention includes the use of probes or primers containing nucleotides differing in the sugar moiety, or otherwise chemically modified, which are able to hydrogen bond along the lines described above.

Thus, in a first aspect, the invention features hybridization assay probes able to distinguish Human Immunodeficiency Virus type 1 from other viruses found in human blood or tissues, and amplification oligonucleotides able to selectively amplify Human Immunodeficiency Virus nucleic acid. Specifically, the probes are nucleotide polymers which hybridize to the nucleic acid region of Human Immunodeficiency Virus type 1 corresponding to bases 763–793 of HIV type 1, (HXB2 isolate GenBank accession number K03455), or any of the regions corresponding to bases 1271–1301, 1358–1387, 1464–1489, 1501–1540, 1813–1845, 2969–2999, 3125–3161, 4148–4170, 4804–4832, 5950–5978, 9496–9523, 510–542, and 624–651; preferably, the oligonucleotide comprises, consists essentially of, or consists of the sequence (reading 5' to 3')

(SEQ ID NO: 1) GACTAGCGGAGGCTAGAAG-GAGAGAGATGGG (SEQ ID NO: 2) GAAGGCTTTCAGCCCAGAAG-TAATACCCATG (SEQ ID NO: 3) ATTTGCATGGCTGCTTGATGTC-CCCCCACT (SEQ ID NO: 4) CTTCCCCTTGGTTCTCTCATCTG-GCC (SEQ ID NO: 5) GTCATCCATCCTATTTGTTCCT-GAAGGGTACTAGTAG (SEQ ID NO: 6) CTCCCTGACATGCTGTCAT-CATTTCTTCTAGTG (SEQ ID NO: 7) GTGGAAGCACATTGTACT-GATATCTAATCCC (SEQ ID NO: 8) GCTCCTCTATTTTTGTTCTATGCT-GCCCTATTTCTAA (SEQ ID NO: 9) CCTTTGTGTGCTGGTACCCATGC (SEQ ID NO:10) CTACTATTCTTTCCCCTGCACTG-TACCCC (SEQ ID NO:11) AAAGCCTTAGGCATCTCCTATG-GCAGGAA (SEQ ID NO:12) GCAGCTGCTTATATGCAGGATCT-GAGGG (SEQ ID NO:13) CAAGGCAAGCTTTATTGAGGCT-TAAGCAGTGGG (SEQ ID NO:14) ATCTCTAGCAGTGGCGCCCGAA-CAGGGA or RNA equivalents thereto (SEQ. ID. Nos. 67–80), or oligonucleotides complementary thereto (SEQ. ID. Nos. 53–66), or RNA equivalents to the oligonucleotides complementary thereto (SEQ. ID. Nos. 81–94).

The oligonucleotides are used with or without a helper probe as described below. The use of helper probes (e.g., SEQ. ID. Nos. 15–18) and complementary oligonucleotides to the helper probes (e.g., SEQ. ID. Nos. 95–98) and RNA equivalents thereto (e.g., SEQ. ID. Nos. 132–140) enhances nucleic acid hybridization.

By "consists essentially of" is meant that the probe is provided as a purified nucleic acid which under stringent hybridizing conditions hybridizes with the target sequence and not with other related target sequences present in either other virus nucleic acids or human nucleic acids. Such a probe may be linked to other nucleic acids which do not affect such hybridization. Generally, it is preferred that the probe is between 15 to 100 (most preferably between 20 and 50) bases in size. It may, however, be provided in a vector.

In a related aspect, the invention features the formation of nucleic acid hybrids formed by the hybridization of the probes of this invention with target nucleic acid under stringent hybridization conditions. Stringent hybridization conditions involve the use 0.05M lithium succinate buffer containing 0.6M LiCl at 60° C. The hybrids are useful because they allow the specific detection of viral nucleic acid.

In another related aspect, the invention features amplification oligonucleotides useful for specific detection of Human Immunodeficiency Virus type 1 in an amplification assay. The amplification oligonucleotides are complementary to conserved regions of HIV genomic nucleic acid and are nucleotide polymers able to hybridize to regions of the nucleic acid of HIV corresponding to HIV-1 HXB2R bases 682–705, 800–822, 1307–1337, 1306–1330, 1315–1340, 1395–1425, 1510–1535, 1549–1572, 1743–1771, 1972–1989, 2868–2889, 3008–3042, 3092–3124, 3209–3235, 4052–4079, 4176–4209, 4169–4206, 4394–4428, 4756–4778, 4835–4857, 4952–4969, 5834–5860, 5979–5999, 9431–9457, 9529–9555, 449–473, 550–577, 578–601, 579–600, 624–646, and 680–703.

Specifically, such amplification oligonucleotides consist, comprise, or consist essentially of those selected from (reading 5' to 3'):

(X)CTCGACGCAGGACTCGGCTTGCTG (SEQ. ID. NO. 19), (X)CTCCCCCGCTTAATACTGACGCT (SEQ. ID. NO. 20), (X)GGCAAATGGTACATCAGGCCATATCACCTAG (SEQ. ID. NO. 21), (X)GGGGTGGCTCCTTCTGATAATGCTG (SEQ. ID. NO. 22), (X)CAGAAGGAGCCACCCCACAAGATTTA (SEQ. ID. NO. 23), (X)GACCATCAATGAGGAAGCTGCAGAATG (SEQ. ID. NO. 24), (X)CCCATTCTGCAGCTTCCTCATTGAT (SEQ. ID. NO. 25), (X)AGTGACATAGCAGGAACTA (SEQ. ID. NO. 26), (X)CCATCCTATTTGTTCCTGAAGGGTAC (SEQ. ID. NO. 27), (X)AGATTTCTCCTACTGGGATAGGT (SEQ. ID. NO. 28), (X)GAAACCTTGTTGAGTCCAAAATGCGAACCC (SEQ. ID. NO. 29), (X)TGTGCCCTTCTTTGCCAC (SEQ. ID. NO. 30), (X)CAGTACTGGATGTGGGTGATGC (SEQ. ID. NO. 31), (X)GTCATGCTACTTTGGAATATTTCTGGTGATCCTTT (SEQ. ID. NO. 32), (X)CAATACATGGATGATTTGTATGTAGGATCTGAC (SEQ. ID. NO. 33), (X)ACCAAAGGAATGGAGGTTCTTTCTGATG (SEQ. ID. NO. 34), (X)GCATTAGGAATCATTCAAGCACAACCAG (SEQ. ID. NO. 35), (X)GCACTGACTAATTTATCTACTTGTTCATTTCCTC (SEQ. ID. NO. 36), (X) GGGATTGGAGGAAATGAACAAGTA-GATAAATTAGTCAG (SEQ. ID. NO. 37), (X)TGTGTACAATCTAGTTGCCATATTCCTGGACTACA (SEQ. ID. NO. 38), (X)CAAATGGCAGTATTCATCCACA (SEQ. ID. NO. 39), (X)GTTTGTATGTCTGTTGCTATTAT (SEQ. ID. NO. 40), (X)CCCTTCACCTTTCCAGAG (SEQ. ID. NO. 41), (X)GAGCCCTGGAAGCATCCAGGAAGTCAG (SEQ. ID. NO. 42), (X)CTTCGTCGCTGTCTCCGCTTC (SEQ. ID. NO. 43), (X)CAAGGGACTTTCCGCTGGGGACTTTCC (SEQ. ID. NO. 44), (X)GTCTAACCAGAGAGACCCAGTACAGGC (SEQ. ID. NO. 45), (X)GTACTGGGTCTCTCTGGTTAGACCA (SEQ. ID. NO. 46), (X)CACACAACAGACGGGCACACACTACTTG (SEQ. ID. NO. 47), (X)CTGAGGGATCTCTAGTTACCAGAGT (SEQ. ID. NO. 48), (X)CTCTGGTAACTAGAGATCCCTCA (SEQ. ID. NO. 49), (X)GTTCGGGCGCCACTGCTAGAGAT (SEQ. ID. NO. 50), (X)GCAAGCCGAGTCCTGCGTCGAGA (SEQ. ID. NO. 51)

and the RNA equivalents thereto (SEQ. ID. Nos. 99–131). Where (X) is nothing or a 5' oligonucleotide sequence that is recognized by an enzyme, including but not limited to the promoter sequence for T7, T3, or SP6 RNA polymerase, which enhances initiation or elongation of RNA transcription by an RNA polymerase. One example of X includes the sequence SEQ. ID. NO. 52: 5'-AATTTAATACGACTCACTATAGGGAGA-3'.

These amplification oligonucleotides are used in a nucleic acid amplification assay such as the polymerase chain reaction or an amplification reaction using RNA polymerase, DNA polymerase and RNase H or its equivalent, as described by Kacian and Fultz, supra, and by Sninsky et al. U.S. Pat. No. 5,079,351, both hereby incorporated by reference herein.

The amplification oligonucleotides and probes of this invention offer a rapid, non-subjective method of identification and quantitation of a sample for specific sequences unique to strains of Human Immunodeficiency Virus type 1.

Other features and advantages of the invention will be apparent from the following description of the preferred embodiments thereof, and from the claims.

DESCRIPTION OF THE PREFERRED EMBODIMENTS

We have discovered particularly useful DNA probes complementary to particular nucleic acid sequences of Human Immunodeficiency Virus type 1. Furthermore, we have successfully used these probes in a specific assay for the detection of Human Immunodeficiency Virus type 1, distinguishing it from the known and presumably most closely related taxonomic or phylogenetic neighbors found in human blood or tissues.

We have also identified particularly useful amplification oligonucleotides which are complementary to the Human Immunodeficiency Virus type 1 nucleic acid, and have used these oligonucleotides, e, as primers or promoter primer combinations (i.e., a primer having a promoter sequence attached), to amplify the nucleic acid of Human Immunodeficiency Virus, allowing its direct detection in a sample.

Useful guidelines for designing amplification oligonucleotides and probes with desired characteristics are described herein. The optimal sites for amplifying and probing contain two, and preferably three, conserved regions greater than about 15 bases in length, within about 350 bases, and preferably within 150 bases, of contiguous sequence. The degree of amplification observed with a set of primers or promotor/primers depends on several factors, including the ability of the oligonucleotides to hybridize to their complementary sequences and their ability to be extended enzymatically. Because the extent and specificity of hybridization reactions are affected by a number of factors, manipulation of those factors will determine the exact sensitivity and specificity of a particular oligonucleotide, whether perfectly complementary to its target or not. The importance and effect of various assay conditions are known to those skilled in the art as described in Hogan et al., EPO Patent Application No. PCT/US87/03009, Publication No. WO 88/03957 entitled "Nucleic Acid Probes for Detection and/or Quantitation of Non-Viral Organisms"; and Milliman, entitled "Nucleic Acid Probes to *Haemophilus influenzae*," U.S. Ser. No. 07/690,788, filed Apr. 25, 1991 assigned to the same assignee as the present application and hereby incorporated by reference herein a continuation of Ser. No. 07/690,788 has issued as U.S. Pat. No. 5,472,843.

The length of the target nucleic acid sequence and, accordingly, the length of the probe sequence can be important. In some cases, there may be several sequences from a particular region, varying in location and length, which will yield probes with the desired hybridization characteristics. In other cases, one sequence may be significantly better than another which differs merely by a single base. While it is possible for nucleic acids that are not perfectly complementary to hybridize, the longest stretch of perfectly homologous base sequence will normally primarily determine hybrid stability. While oligonucleo- tide probes of different lengths and base composition may be used, oligonucleotide probes preferred in this invention are between about 10 to 50 bases in length and are sufficiently homologous to the target nucleic acid to hybridize under stringent hybridization conditions. We have found that optimal primers have target-binding regions of 18–38 bases, with a predicted Tm (melting temperature) to target of about 65° C.

Amplification oligonucleotides or probes should be positioned so as to minimize the stability of the oligomer:non-target (i.e., nucleic acid with similar sequence to target nucleic acid) nucleic acid hybrid. It is preferred that the amplification oligomers and detection probes are able to distinguish between target and non-target sequences. In designing probes, the differences in these Tm values should be as large as possible (e.g., at least 2° C. and preferably 5° C.).

Regions of the nucleic acid which are known to form strong internal structures inhibitory to hybridization are less preferred. Examples of such structures include hairpin loops. Likewise, probes with extensive self-complementarity should be avoided.

The degree of non-specific extension (primer-dimer or non-target copying) can also affect amplification efficiency, therefore primers are selected to have low self- or cross-complementarity, particularly at the 3' ends of the sequence. Long homopolymer tracts and high GC content are avoided to reduce spurious primer extension. Commercial computer programs are available to aid in this aspect of the design. Available computer programs include MacDNASIS™ 2.0 (Hitachi Software Engineering American Ltd.) and OLIGO® ver. 4.1 (National Bioscience).

Hybridization is the association of two single strands of complementary nucleic acid to form a hydrogen bonded double strand. It is implicit that if one of the two strands is wholly or partially involved in a hybrid that it will be less able to participate in formation of a new hybrid. By designing a probe so that a substantial portion of the sequence of interest is single stranded, the rate and extent of hybridization may be greatly increased. If the target is an integrated genomic sequence then it will naturally occur in a double stranded form, as is the case with the product of the polymerase chain reaction (PCR). These double-stranded targets are naturally inhibitory to hybridization with a probe and require denaturation prior to the hybridization step. Finally, there can be intramolecular and intermolecular hybrids formed within a probe if there is sufficient self complementarity. Such structures can be avoided through careful probe design. Commercial computer programs are available to search for this type of interaction. Available computer programs include MacDNASIS™ 2.0 (Hitachi Software Engineering American Ltd.) and OLIGO® ver. 4.1 (National Bioscience).

Once synthesized, selected oligonucleotide probes may be labelled by any of several well known methods. 2 J. Sambrook, E. F. Fritsch and T. Maniatis, *Molecular Cloning* 11 (2d ed. 1989). Useful labels include radioisotopes as well as non-radioactive reporting groups. We currently prefer to use acridinium esters.

Oligonucleotide/target hybrid melting temperature may be determined by isotopic methods well known to those skilled in the art. It should be noted that the Tm for a given hybrid will vary depending on the hybridization solution being used. Sambrook, et al. supra.

Rate of hybridization may be measured by determining the $C_0t_{1/2}$. The rate at which a probe hybridizes to its target is a measure of the thermal stability of the target secondary structure in the probe region. The standard measurement of hybridization rate is the $C_0t_{1/2}$ which is measured as moles of nucleotide per liter times seconds. Thus, it is the concentration of probe times the time at which 50% of maximal hybridization occurs at that concentration. This value is determined by hybridizing various amounts of probe to a constant amount of target for a fixed time. The $C_0t_{1/2}$, is found graphically by standard procedure.

The following examples set forth oligonucleotide probes complementary to a unique nucleic acid sequence from a target organism, and their use in a hybridization assay.

EXAMPLES

Probes specific for Human Immunodeficiency Virus type 1 were identified by comparison of sequences obtained from the published database GenBank. Sequences ID Nos. 1–12 were characterized and shown to be specific for Human Immunodeficiency virus type 1. Phylogenetically near neighbors including Human Immunodeficiency Virus type 2, Human T-cell Leukemia Virus type 1 and Human T-Cell Leukemia Virus type 2 were used as comparisons with the sequence of Human Immunodeficiency Virus Type 1.

Example 1
Probes for HIV

A hybridization protection assay was used to demonstrate the reactivity and specificity of the probes for Human Immunodeficiency Virus type 1. The probes were first synthesized with a non-nucleotide linker, then labelled with a chemiluminescent acridinium ester (AE) as described by Arnold, et al., PCT/US88/03361, Publication No. WO 89/02896 entitled "Acridinium Ester Labeling and Purification of Nucleotide Probes," hereby incorporated by reference herein. The acridinium ester attached to an unhybridized probe is susceptible to hydrolysis and rendered non-chemiluminescent under mild alkaline conditions. However, the acridinium ester attached to hybridized probe is relatively resistant to hydrolysis. Thus, it is possible to assay for hybridization of acridinium ester-labelled probe by incubation with an alkaline buffer, followed by detection of chemiluminescence in a luminometer. Results are given in Relative Light Units (RLU); the quantity of photons emitted by the labelled-probe measured by the luminometer.

In the following experiment, DNA prepared from clones containing full or partial sequences of the target viruses was assayed. An example of a method for preparing the DNA from clones is provided by Sambrook et al, supra. The source of DNA for the clones was as follows; Human Immunodeficiency Virus type 1, BH10 (L. Ratner et al., *Nature* 312:277–284. 1985); Human Immunodeficiency Virus type 2 NIHZ (J. F. Zagury, et al., *Proc. Natl. Acad. Sci. USA* 85:5941–5945. 1988), Human T-cell leukemia virus type 1 pMT-2, (M. Clarke et al. *Nature* 305:60–62. 1983); Human T-cell leukemia virus type 2 (K. Shimotohmo et al. *Proc. Natl. Acad. Sci. USA* 82:3101–3105. 1985); and Human Hepatitis B Virus serotype ADW, obtained from ATCC(# 45020). Target in 50 µl of 10 mM N-2-hydroxyethelpiperazine-N'-2-ethanesulfonic acid (HEPES), 10 mM ethylenediaminetetraacetic acid (EDTA), 1% lithium lauryl sulfate, pH 7.4, was denatured at 95° C. for 5 min, cooled on wet ice, and 0.04 pmol of probe in 50 µl of 0.1M lithium succinate buffer, pH 4.7, 2% (w/v) lithium lauryl sulfate, 1.2M lithium chloride, 10 mM'EDTA and 20 mM ethyleneglycol-bis-(beta-aminoethyl ether) N,N,N',N'-tetraacetic acid (EGTA) was added. Hybridization was carried out at 60° C. for 10 min, followed by addition of 300 µl of 0.6M sodium borate pH 8.5, 1% Triton X-100 and a second incubation at 60° C. for 6 min to hydrolyze the AE on unhybridized probe. Samples were cooled in ice water for 1 min, placed at room temperature for another 3 min, and then analyzed in a LEADER 1 luminometer equipped with automatic injection of detection reagent I (containing 0.1% hydrogen peroxide and 1 mM nitric acid) and detection reagent II (containing 1N sodium hydroxide and a surfactant component). Some of the hybridization reactions were enhanced with the addition of 4 pmol of unlabelled "helper probe" as disclosed in Hogan et al., U.S. Pat. No. 5,030,557 entitled "Means and Methods for Enhancing Nucleic Acid Hybridization", hereby incorporated by reference herein. An RLU value greater than 5,000 RLU was a positive result; less than 5,000 RLU was a negative result.

The following data (Table 1) show that the probes do not cross react with viral DNA from closely related viruses found in human blood or tissues. The samples also gave a positive signal when tested with a probe specific to each target, thereby confirming sample adequacy.

TABLE 1

Hybridization Assay with HIV-1 probes.

| Probe Sequence No: | Target: | | | | | | |
|---|---|---|---|---|---|---|---|
| | 1 | 2 | 3 | 4 | 5 | 6 | 7 |
| 1 | 179,166 | 482 | 500 | 496 | 190 | 496 | 470 |
| 2 | 14,992 | 563 | 394 | 377 | 409 | 383 | 465 |
| 4 | 61,691 | 2,818 | 750 | 695 | 686 | 702 | 642 |
| 6 | 28,038 | 546 | 408 | 375 | 356 | 369 | 372 |
| 7 | 27,407 | 640 | 401 | 252 | 366 | 343 | 359 |
| 8 | 45,868 | 1,432 | 395 | 392 | 386 | 401 | 404 |
| 9 | 15,971 | 721 | 280 | 268 | 261 | 274 | 284 |
| 10 | 59,007 | 714 | 264 | 280 | 284 | 272 | 567 |
| 11 | 25,856 | 4,641 | 3,598 | 3,736 | 3,711 | 3,855 | 3,388 |
| 12 | 140,691 | 1,846 | 602 | 694 | 531 | 534 | 1,236 |

Target 1=HIV-1 BH10 isolate 9 Kb SstI fragment, Target 2=Human Immunodeficiency Virus Type 2 (NIHZ isolate) 9 Kb NaeI fragment, Target 3=Human T-cell leukemia virus type 1 (pMT-2) 5' 4.6 Kb SstI-BamHI fragment; Target 4=Human T-cell leukemia virus type 1 3' 4.4 Kb XbaI-SstI fragment, Target 5=Human T-cell leukemia virus type 2 3.5 Kb BamHI fragment, Target 6=Human T-cell leukemia virus type 2 5 Kb BamHI fragment, Target 7=Human Hepatitis B virus serotype ADW 1.3, 1.8 Kb BamHI fragments.

The above data confirm that the novel probes herein disclosed and claimed are capable of distinguishing Human Immunodeficiency Virus type 1 from these viruses found in human blood.

Example 2
Amplification of HIV by PCR

To demonstrate the reactivity of the primers and probes for Human Immunodeficiency Virus type 1, the following experiment was performed. Zero, 20, or 100 copies of plasmid DNA containing Human Immunodeficiency Virus DNA was linearized with a restriction endonuclease, and added to amplification reactions containing 50 pmol of each primer, 10 mM Tris HCl pH 8, 50 mM KCl, 1.25 mM MgCl$_2$, 0.25 mM each of dATP, dTTP, dCTP, dGTP, and 2.5 U Taq DNA polymerase in 50 µl. The reactions were incubated at 95° C. for 1–2 min, and then cycled 35 times at 55° C. for 15 sec, 72° C. for 30 sec, and 95° C. for 20 sec in a Perkin-Elmer 9600 thermocycler or 55° C. for 30 sec, 72° C. for 60 sec, and 95° C. for 60 sec in a Perkin-Elmer 48 well thermocycler. Following cycling, the reactions were incubated at 72° C. for 6–7 min and stored at 4° C. Ten µl of the product was analyzed by hybridization protection assay with 0.04 pmol of labeled probe. The data are shown in Table 2. RLU greater than 7,000 is considered a positive result.

TABLE 2

Amplification of Human Immunodeficiency Virus Type 1 by PCR

| Primer Sequence ID Nos: | Probe Sequence ID. No. | Sample RLU | | |
|---|---|---|---|---|
| | | 0 c | 20 c | 100 c |
| 19/20* | 1 | 886 | 827,202 | 723,008 |
| 21/22* | 2 | 2,677 | 24,030 | 48,521 |
| *23/25 | 3 | 370 | 144,082 | 603,456 |
| *24/27 | 4 | 4,042 | 81,052 | 163,355 |
| *26/28 | 5 | 263 | 273,623 | 593,022 |
| *29/30 | E | 1,008 | 328,736 | 366,590 |
| *31/32 | 7 | 3,394 | 73,690 | 86,168 |
| *33/34 | 8 | 1,648 | 7,152 | 24,027 |
| *35/36 | 9 | 560 | 82,980 | 145,681 |
| *39/40 | 10 | 810 | 279,079 | 299,815 |
| *39/41 | 10 | 886 | 362,914 | 427,500 |
| 42/43* | 11 | 5,830 | 680,788 | 1,939,372 |
| *44/45 | 12 | 1,387 | 21,428 | 130,709 |

The starred (*) primers had the sequence 5'-AATTTAATACGACTCACTATAGGGAGA-3' attached to the 5' end of the primer. 0 c=0 copies of HIV DNA, 20 c=20 copies of HIV DNA, 100 c=100 copies of HIV DNA. Probe 1 was used in the presence of unlabeled helper probe SEQ. ID. No. 15. Probe 7 was used in the presence unlabeled helper probe SEQ. ID. No. 16. Probe 10 was used in the presence of unlabeled helper probe SEQ. ID. No. 17. Probe 12 was used in the presence of unlabeled helper probe SEQ. ID. No. 18. As the copy number increased, RLU increased. Thus, the primers of the present invention were able to successfully amplify, by PCR, HIV type 1 target sequences which were detected using the probes of the present invention.

Example 3
Patient samples

In this example, patient samples containing lysate prepared from 200,000 Ficoll-Hypaque purified white blood cells from individuals known to be infected with HIV type 1 or an individual not infected with HIV type 1 (negative) were analyzed as described in Example 2. These cells were prepared as described in Ryder and Kacian, entitled "Preparation of nucleic acid from blood," U.S. Ser. No. 07/898,785, filed Jun. 12, 1992. The results are shown in Table 3.

TABLE 3

PCR Assay

| Primer Sequence ID Nos: | Probe Sequence ID. No. | Sample RLU | | |
|---|---|---|---|---|
| | | Patient 1 | Patient 2 | Negative |
| 19/20* | 1 | 27,616 | 71,981 | 886 |
| 21/22* | 2 | 34,949 | 35,483 | 565 |
| *23/25 | 3 | 45,230 | 93,529 | 455 |
| *24/27 | 4 | 2,355 | 25,329 | 1,052 |
| *26/28 | 5 | 22,345 | 26,014 | 369 |
| *31/32 | 7 | 200,418 | 130,486 | 481 |
| *33/34 | 8 | 43,993 | 40,389 | 705 |
| *39/40 | 10 | 36,310 | 50,838 | 976 |
| *39/41 | 10 | 55,582 | 98,504 | 993 |
| 42/43* | 11 | 99,028 | 207,605 | 6,057 |
| *44/45 | 12 | 55,082 | 80,388 | 1,496 |

The starred (*) primers had the sequence 5'-AATTTAATACGACTCACTATAGGGAGA-3' attached to the 5' end of the primer. The primers of the present invention were able to amplify by PCR HIV type 1 target sequences present in individuals infected with HIV. The amplified target sequences were detected by the probes of the present invention. Thus, individuals containing HIV type 1 and an individual not containing HIV type 1 were correctly identified.

Example 4

Non-PCR Amplification

To show that the amplification oligomers also work in a transcription based amplification assay, 0, 2,000, or 20,000 copies of plasmid DNA containing HIV type 1 was linearized using a restriction endonuclease, and heated to 95° C. for two min and cooled to 37° C. for 1 min. Following addition of 800 U of MMLV reverse transcriptase the reactions were incubated for 12 min at 37° C., heated to 95° C. for two min, and cooled to 37° C. for one min. 800 U of MMLV reverse transcriptase and 400 U of T7 RNA polymerase were added and the reactions were incubated for 3 hr at 37° C. The final amplification conditions were 70 mM Tris HCl, pH 8, 35 mM KCp, 15 mM KOH neutralized N-acetylcysteine, 6 mM rGTP, 4 mM rCTP, 4 mM rATP, 4 mM rUTP, 1 mM each of dTTP, dATP, dCTP and dGTP, and 22 mM $MgCl_2$ in 100 µl. Ten µl of each reaction was mixed with 40 µl of water and assayed as described for Table 1 except that the hybridization buffer contained 20 mM aldrithiol. The results in RLU are shown in Table 4.

TABLE 4

Transcription-Based Amplification Assay

| Primers Sequence ID Nos: | Probe Sequence ID. No. | RLU | | |
|---|---|---|---|---|
| | | 0 c | 2,000 c | 20,000 c |
| 19/20* | 1 | 681 | 24,170 | 190,536 |
| 21/22* | 2 | 793 | 62,476 | 523,770 |
| *23/25 | 3 | 2,239 | 812,577 | 1,126,045 |
| *24/27 | 4 | 1,901 | 160,274 | 780,351 |
| *26/28 | 5 | 2,555 | 877,893 | 1,167,756 |
| *29/30 | 6 | 868 | 299,255 | 880,119 |
| *31/32 | 7 | 871 | 129,732 | 969,034 |
| *33/34 | 8 | 710 | 134,887 | 986,266 |
| *35/36 | 9 | 884 | 128,981 | 1,021,865 |
| *39/40 | 10 | 1,597 | 375,629 | 478,883 |
| *39/41 | 10 | 1,264 | 499,304 | 495,509 |
| *44/45 | 12 | 2,426 | 41,684 | 542,339 |

The starred (*) primers had the sequence 5'-AATTTAATACGACTCACTATAGGGAGA-3' attached to the 5' end of the primer. Probe 1 was used in the presence of unlabelled helper probe SEQ. ID. No. 15. Probe 7 was used in the presence of unlabelled helper probe SEQ. ID. No. 16, probe 10 was used in the presence of unlabelled helper probe SEQ. ID. No. 17, and probe 12 was used in the presence of unlabelled helper probe SEQ. ID. No. 18. 0 c=0 copies of HIV DNA, 2,000 c=2,000 copies of HIV DNA, 20,000 c=20,000 copies of HIV DNA.

As the copy number increased RLU also increased. Thus, the primers of the present invention can be used to amplify HIV type 1 target sequences using a transcription based amplification assay and the amplified target sequences can be detected using the probes of the present invention.

Example 5

This example demonstrates the ability of probes for Human Immunodeficiency Virus type 1 to detect low levels of target oligomer produced in a transcription based amplification assay. Zero or 10 copies of plasmid DNA containing HIV type I sequence was linearized using a restriction endonuclease, heated in the presence of 1 µg of human DNA to 95° C. for eight minutes, and then cooled to 42° C. for six minutes. Amplification was carried out at 42° C. for two hours using 800 U MMLV reverse transcriptase and 400 U of T7 RNA polymerase, in the following reaction mix: 50 mM Tris HCl pH 8, 17.5 mM $MgCl_2$, 0.05 mM zinc acetate, 10% glycerol, 6.25 mM rGTP, 2.5 mM rCTP, 6.25 mM rATP, 2.5 mM rUTP, 0.2 mM dTTP, 0.2 mM dATP, 0.2 mM, 0.2 mM dCTP and 0.2 mM dGTP. Primer SEQ ID NOs. 26, 28, and 41 were used at a concentration of 30 pmol, primer SEQ ID NO. 39 was used at a concentration of 15 pmol. The entire reaction was analyzed using the hybridization protection assay with 0.04 pmol of probe in 100 µl of the hybridization buffer (supplemented with 20 mM aldrithiol) as described in Example 1. Probe SEQ ID NO. 10 was hybridized in the presence of 2 pmol unlabeled helper SEQ ID NO. 17.

TABLE 5

Low Level Transcription-Based Amplification Assay

| Primers SEQ ID NOs. | Probe SEQ | RLU | |
|---|---|---|---|
| | | 0 copies | 10 copies |
| *26/28 | 5 | 1,293 | 64,639 |
| *39/40 | 10 | 2,143 | 564,485 |

The 10 copy values represent the average of ten replicates. The starred (*) primers had the sequence 5'-AATTTAATACGACTCACTATAGGGAGA-3' attached to the 5' end of the primer.

Other embodiments are within the following claims.

We claim:

1. A method for determining whether HIV-1 is present in a sample and distinguishing the presence of HIV-1 from HIV-2 comprising the steps of,
   a) contacting said sample with a hybridization assay detection probe comprising a nucleotide base sequence for specifically detecting an HIV-1 target sequence selected from the group consisting of SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 53, SEQ ID NO 54, SEQ ID NO 55, SEQ ID NO 56, SEQ ID NO 57, SEQ ID NO 58, SEQ ID NO 59, SEQ ID NO 60, SEQ ID NO 61, SEQ ID NO 62, SEQ ID NO 63, SEQ ID NO 64, SEQ ID NO 65, SEQ ID NO 66, SEQ ID NO 67, SEQ ID NO 68, SEQ ID NO 69, SEQ ID NO 70, SEQ ID NO 71, SEQ ID NO 72, SEQ ID NO 73, SEQ ID NO 74, SEQ ID NO 75, SEQ ID NO 76, SEQ ID NO 77, SEQ ID NO 78, SEQ ID No 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, and SEQ ID NO 94; and
   b) measuring the ability of said detection probe to detect the presence of said target sequence as an indication that HIV-1 and not HIV-2 is present in said sample.

2. The method of claim 1, wherein said target sequence is selected from the group consisting of SEQ ID NO 1, SEQ ID NO 53, SEQ ID NO 67, and SEQ ID NO 81.

3. The method of claim 1, wherein said target sequence is selected from the group consisting of SEQ ID NO 2, SEQ ID NO 54, SEQ ID NO 68, and SEQ ID NO 82.

4. The method of claim 1, wherein said target sequence is selected from the group consisting of SEQ ID NO 3, SEQ ID NO 55, SEQ ID NO 69, and SEQ ID NO 83.

5. The method of claim 1, wherein said target sequence is selected from the group consisting of SEQ ID NO 4, SEQ ID NO 56, SEQ ID NO 70, and SEQ ID NO 84.

6. The method of claim 1, wherein said target sequence is selected from the group consisting of SEQ ID NO 5, SEQ ID NO 57, SEQ ID NO 71, and SEQ ID NO 85.

7. The method of claim 90, wherein said target sequence is selected from the group consisting of SEQ ID NO 6, SEQ ID NO 58, SEQ ID NO 72, and SEQ ID NO 86.

8. The method of claim 1, wherein said target sequence is selected from the group consisting of SEQ ID NO 7, SEQ ID NO 59, SEQ ID NO 73, and SEQ ID NO 87.

9. The method of claim 1, wherein said target sequence is selected from the group consisting of SEQ ID NO 8, SEQ ID NO 60, SEQ ID NO 74, and SEQ ID NO 88.

10. The method of claim 1, wherein said target sequence is selected from the group consisting of SEQ ID NO 9, SEQ ID NO 61, SEQ ID NO 75, and SEQ ID NO 89.

11. The method of claim 1, wherein said target sequence is selected from the group consisting of SEQ ID NO 10, SEQ ID NO 62, SEQ ID NO 76, and SEQ ID NO 90.

12. The method of claim 1, wherein said target sequence is selected from the group consisting of SEQ ID NO 11, SEQ ID NO 63, SEQ ID NO 77, and SEQ ID NO 91.

13. The method of claim 1, wherein said target sequence is selected from the group consisting of SEQ ID NO 12, SEQ ID NO 64, SEQ ID NO 78, and SEQ ID NO 92.

14. The method of claim 1, wherein said target sequence is selected from the group consisting of SEQ ID NO 13, SEQ ID NO 65, SEQ ID NO 79, and SEQ ID NO 93.

15. The method of claim 1, wherein said target sequence is selected from the group consisting of SEQ ID NO 14, SEQ ID NO 66, SEQ ID NO 80, and SEQ ID NO 94.

16. A method for determining whether HIV-1 is present in a sample and distinguishing the presence of HIV-1 from HIV-2 comprising the steps of, a) contacting said sample with a hybridization assay detection probe comprising a nucleotide base sequence selected from the group consisting of SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 53, SEQ ID NO 54, SEQ ID NO 55, SEQ ID NO 56, SEQ ID NO 57, SEQ ID NO 58, SEQ ID NO 59, SEQ ID NO 60, SEQ ID NO 61, SEQ ID NO 62, SEQ ID NO 63, SEQ ID NO 64, SEQ ID NO 65, SEQ ID NO 66, SEQ ID NO 67, SEQ ID NO 68, SEQ ID NO 69, SEQ ID NO 70, SEQ ID NO 71, SEQ ID NO 72, SEQ ID NO 73, SEQ ID NO 74, SEQ ID NO 75, SEQ ID NO 76, SEQ ID NO 77, SEQ ID NO 78, SEQ ID NO 79, SEQ ID NO 80, SEQ ID NO 81, SEQ ID NO 82, SEQ ID NO 83, SEQ ID NO 84, SEQ ID NO 85, SEQ ID NO 86, SEQ ID NO 87, SEQ ID NO 88, SEQ ID NO 89, SEQ ID NO 90, SEQ ID NO 91, SEQ ID NO 92, SEQ ID NO 93, and SEQ ID NO 94;

wherein under hybridization assay conditions said detection probe hybridizes to a nucleic acid from HIV-1 to form a detectable probe:target duplex and does not hybridize to non-target nucleic acid from Human Immunodeficiency Virus type 2, Human T-Cell leukemia virus type 1, Human T-cell virus type 2, and Human Hepatitis B virus serotype ADW to form a detectable probe:non-target duplex indicating the presence of said non-target nucleic acid under said conditions, b) measuring the ability of said detection probe to hybridize to nucleic acid present in said sample as an indication that HIV-1 and not HIV-2 is present in said sample.

17. The method of claim 16, wherein said nucleotide base sequence is selected from the group consisting of SEQ ID NO 1, SEQ ID NO 53, SEQ ID NO 67, and SEQ ID NO 81.

18. The method of claim 17, wherein said detection probe consists of an optionally labeled oligonucleotide, provided that the base sequence of said optionally labeled oligonucleotide consists of a detection probe nucleotide base sequence selected from the group consisting of SEQ ID NO 1, SEQ ID NO 53, SEQ ID NO 67, and SEQ ID NO 81.

19. The method of claim 18, wherein said detection probe comprises a reporter group label.

20. The method of claim 19, wherein said step (a) further comprises providing to said sample one or more helper oligonucleotides consisting of a nucleotide base sequence selected from the group consisting of SEQ ID NO 15, SEQ ID NO 95, SEQ ID NO 132, and SEQ ID NO 136.

21. The method of claim 19, further comprising the step of amplifying HIV-1 nucleic acid, if present, using a first amplification oligonucleotide comprising a sequence selected from the group consisting of SEQ ID NO 19 and SEQ ID NO 99; and a second amplification oligonucleotide comprising a sequence selected from the group consisting of SEQ ID NO 20 and SEQ ID NO 100.

22. The method of claim 21, wherein said first amplification oligonucleotide consists of the sequence of SEQ ID NO 20 and a sequence recognized by an RNA polymerase joined to the 5' end of SEQ ID NO 20; said second amplification oligonucleotide consists of the sequence of SEQ ID NO 19; and said detection probe nucleotide base sequence consists of the sequence of SEQ ID NO 1.

23. The method of claim 16, wherein said nucleotide base sequence is selected from the group consisting of SEQ ID NO 2, SEQ ID NO 54, SEQ ID NO 68, and SEQ ID NO 82.

24. The method of claim 23, wherein said detection probe consists of an optionally labeled oligonucleotide, provided that the base sequence of said optionally labeled oligonucleotide consists of a detection probe nucleotide base sequence selected from the group consisting of SEQ ID NO 2, SEQ ID NO 54, SEQ ID NO 68, and SEQ ID NO 82.

25. The method of claim 24, wherein said detection probe comprises a reporter group label.

26. The method of claim 25, further comprising the step of amplifying HIV-1 nucleic acid, if present, using a first amplification oligonucleotide comprising a sequence selected from the group consisting of SEQ ID NO 21 and SEQ ID NO 101; and a second amplification oligonucleotide comprising a sequence selected from the group consisting of SEQ ID NO 22 and SEQ ID NO 102.

27. The method of claim 26, wherein said first amplification oligonucleotide consists of the sequence of SEQ ID NO 21; said second amplification oligonucleotide consists of the sequence of SEQ ID NO 22 and a sequence recognized by an RNA polymerase joined to the 5' end of SEQ ID NO 22; and said detection probe nucleotide base sequence consists of the sequence of SEQ ID NO 2.

28. The method of claim 16, wherein said nucleotide base sequence is selected from the group consisting of SEQ ID NO 3, SEQ ID NO 55, SEQ ID NO 69, and SEQ ID NO 83.

29. The method of claim 28, wherein said detection probe consists of an optionally labeled oligonucleotide, provided that the base sequence of said optionally labeled oligonucleotide consists of a detection probe nucleotide base sequence selected from the group consisting of SEQ ID NO 3, SEQ ID NO 55, SEQ ID NO 69, and SEQ ID NO 83.

30. The method of claim 29, wherein said detection probe comprises a reporter group label.

31. The method of claim 30, further comprising the step of amplifying HIV-1 nucleic acid, if present, using a first amplification oligonucleotide comprising a sequence selected from the group consisting of SEQ ID NO 23 and SEQ ID NO 103; and a second amplification oligonucleotide comprising a sequence selected from the group consisting of SEQ ID NO 25 and SEQ ID NO 105.

32. The method of claim 31, wherein said first amplification oligonucleotide consists of the sequence of SEQ ID NO 23 and a sequence recognized by an RNA polymerase joined to the 5' end of SEQ ID NO 23; said second amplification oligonucleotide consists of the sequence of SEQ ID NO 25; and said detection probe nucleotide base sequence consists of the sequence of SEQ ID NO 3.

33. The method of claim 16, wherein said nucleotide base sequence is selected from the group consisting of SEQ ID NO 4, SEQ ID NO 56, SEQ ID NO 70, and SEQ ID NO 84.

34. The method of claim 33, wherein said detection probe consists of an optionally labeled oligonucleotide, provided that the base sequence of said optionally labeled oligonucleotide consists of a detection probe nucleotide base sequence selected from the group consisting of SEQ ID NO 4, SEQ ID NO 56, SEQ ID NO 70, and SEQ ID NO 84.

35. The method of claim 34, wherein said detection probe comprises a reporter group label.

36. The method of claim 35, further comprising the step of amplifying HIV-1 nucleic acid, if present, using a first amplification oligonucleotide comprising a sequence selected from the group consisting of SEQ ID NO 24 and SEQ ID NO 104; and a second amplification oligonucleotide comprising a sequence selected from the group consisting of SEQ ID NO 27 and SEQ ID NO 107.

37. The method of claim 36, wherein said first amplification oligonucleotide consists of the sequence of SEQ ID NO 27; said second amplification oligonucleotide consists of the sequence of SEQ ID NO 24 and a sequence recognized by an RNA polymerase joined to the 5' end of SEQ ID NO 24; and said detection probe nucleotide base sequence consists of the sequence of SEQ ID NO 4.

38. The method of claim 16, wherein said nucleotide base sequence is selected from the group consisting of SEQ ID NO 5, SEQ ID NO 57, SEQ ID NO 71, and SEQ ID NO 85.

39. The method of claim 38, wherein said detection probe consists of an optionally labeled oligonucleotide, provided that the base sequence of said optionally labeled oligonucleotide consists of a detection probe nucleotide base sequence selected from the group consisting of SEQ ID NO 5, SEQ ID NO 57, SEQ ID NO 71, and SEQ ID NO 85.

40. The method of claim 39, wherein said detection probe comprises a reporter group label.

41. The method of claim 40, further comprising the step of amplifying HIV-1 nucleic acid, if present, using a first amplification oligonucleotide comprising a sequence selected from the group consisting of SEQ ID NO 26 and SEQ ID NO 106; and a second amplification oligonucleotide comprising a sequence selected from the group consisting of SEQ ID NO 28 and SEQ ID NO 108.

42. The method of claim 41, wherein said first amplification oligonucleotide consists of the sequence of SEQ ID NO 26 and a sequence recognized by an RNA polymerase joined to the 5' end of SEQ ID NO 26; said second amplification oligonucleotide consists of the sequence of SEQ ID NO 28; and said detection probe nucleotide base sequence consists of the sequence of SEQ ID NO 5.

43. The method of claim 16, wherein said nucleotide base sequence is selected from the group consisting of SEQ ID NO 6, SEQ ID NO 58, SEQ ID NO 72, and SEQ ID NO 86.

44. The method of claim 43, wherein said detection probe consists of an optionally labeled oligonucleotide, provided that the base sequence of said optionally labeled oligonucleotide consists of a detection probe nucleotide base sequence selected from the group consisting of SEQ ID NO 6, SEQ ID NO 58, SEQ ID NO 72, and SEQ ID NO 86.

45. The method of claim 44, wherein said detection probe comprises a reporter group label.

46. The method of claim 45, further comprising the step of amplifying HIV-1 nucleic acid, if present, using a first amplification oligonucleotide comprising a sequence selected from the group consisting of SEQ ID NO 29 and SEQ ID NO 109; and a second amplification oligonucleotide comprising a sequence selected from the group consisting of SEQ ID NO 30 and SEQ ID NO 110.

47. The method of claim 46, wherein said first amplification oligonucleotide consists of the sequence of SEQ ID NO 29 and a sequence recognized by an RNA polymerase joined to the 5' end of SEQ ID NO 29; said second amplification oligonucleotide consists of the sequence of SEQ ID NO 30; and said detection probe nucleotide base sequence consists of the sequence of SEQ ID NO 6.

48. The method of claim 16, wherein said nucleotide base sequence is selected from the group consisting of SEQ ID NO 7, SEQ ID NO 59, SEQ ID NO 73, and SEQ ID NO 87.

49. The method of claim 48, wherein said detection probe consists of an optionally labeled oligonucleotide, provided that the base sequence of said optionally labeled oligonucleotide consists of a detection probe nucleotide base sequence selected from the group consisting of SEQ ID NO 7, SEQ ID NO 59, SEQ ID NO 73, and SEQ ID NO 87.

50. The method of claim 49, wherein said detection probe comprises a reporter group label.

51. The method of claim 50, wherein said step (a) further comprises providing to said sample one or more helper oligonucleotides consisting of a nucleotide base sequence selected from the group consisting of SEQ ID NO 16, SEQ ID NO 96, SEQ ID NO 133, and SEQ ID NO 137.

52. The method of claim 50, wherein said method further comprises the step of amplifying HIV-1 nucleic acid, if present, using a first amplification oligonucleotide comprising a sequence selected from the group consisting of SEQ ID NO 31 and SEQ ID NO 111; and a second amplification oligonucleotide comprising a sequence selected from the group consisting of SEQ ID NO 32 and SEQ ID NO 112.

53. The method of claim 52, wherein said first amplification oligonucleotide consists of the sequence of SEQ ID NO 31 and a sequence recognized by an RNA polymerase joined to the 5' end of SEQ ID NO 31; said second amplification oligonucleotide consists of the sequence of SEQ ID NO 32; and said detection probe nucleotide base sequence consists of the sequence of SEQ ID NO 7.

54. The method of claim 16, wherein said nucleotide base sequence is selected from the group consisting of SEQ ID NO 8, SEQ ID NO 60, SEQ ID NO 74, and SEQ ID NO 88.

55. The method of claim 54, wherein said detection probe consists of an optionally labeled oligonucleotide, provided that the base sequence of said optionally labeled oligonucleotide consists of a detection probe nucleotide base sequence selected from the group consisting of SEQ ID NO 8, SEQ ID NO 60, SEQ ID NO 74, and SEQ ID NO 88.

56. The method of claim 55, wherein said detection probe comprises a reporter group label.

57. The method of claim 56, further comprising the step of amplifying HIV-1 nucleic acid, if present, using a first amplification oligonucleotide comprising a sequence selected from the group consisting of SEQ ID NO 33 and SEQ ID NO 113; and a second amplification oligonucleotide comprising a sequence selected from the group consisting of SEQ ID NO 34 and SEQ ID NO 114.

58. The method of claim 57, wherein said first amplification oligonucleotide consists of the sequence of SEQ ID NO 33 and a sequence recognized by an RNA polymerase joined to the 5' end of SEQ ID NO 33; said second amplification oligonucleotide consists of the sequence of SEQ ID NO 34; and said detection probe nucleotide base sequence consists of the sequence of SEQ ID NO 8.

59. The method of claim 16, wherein said nucleotide base sequence is selected from the group consisting of SEQ ID NO 9, SEQ ID NO 61, SEQ ID NO 75, and SEQ ID NO 89.

60. The method of claim 59, wherein said detection probe consists of an optionally labeled oligonucleotide, provided that the base sequence of said optionally labeled oligonucleotide consists of a detection probe nucleotide base sequence selected from the group consisting of SEQ ID NO 9, SEQ ID NO 61, SEQ ID NO 75, and SEQ ID NO 89.

61. The method of claim 60, wherein said detection probe comprises a reporter group label.

62. The method of claim 61, further comprising the step of amplifying HIV-1 nucleic acid, if present, using a first amplification oligonucleotide comprising a sequence selected from the group consisting of SEQ ID NO 35 and SEQ ID NO 115; and a second amplification oligonucleotide comprising a sequence selected from the group consisting of SEQ ID NO 36 and SEQ ID NO 116.

63. The method of claim 62, wherein said first amplification oligonucleotide consists of the sequence of SEQ ID NO 35 and a sequence recognized by an RNA polymerase joined to the 5' end of SEQ ID NO 35; said second amplification oligonucleotide consists of the sequence of SEQ ID NO 36; and said detection probe nucleotide base sequence consists of the sequence of SEQ ID NO 9.

64. The method of claim 16, wherein said nucleotide base sequence is selected from the group consisting of SEQ ID NO 10, SEQ ID NO 62, SEQ ID NO 76, and SEQ ID NO 90.

65. The method of claim 64, wherein said detection probe consists of an optionally labeled oligonucleotide, provided that the base sequence of said optionally labeled oligonucleotide consists of a detection probe nucleotide base sequence selected from the group consisting of SEQ ID NO 10, SEQ ID NO 62, SEQ ID NO 76, and SEQ ID NO 90.

66. The method of claim 65, wherein said detection probe comprises a reporter group label.

67. The method of claim 66, wherein said step (a) further comprises providing to said sample one or more helper oligonucleotides consisting of a nucleotide base sequence selected from the group consisting of SEQ ID NO 17, SEQ ID NO 97, SEQ ID NO 134, and SEQ ID NO 138.

68. The method of claim 66, further comprising the step of amplifying HIV-1 nucleic acid, if present, using a first amplification oligonucleotide comprising a sequence selected from the group consisting of SEQ ID NO 39 and SEQ ID NO 119; and a second amplification oligonucleotide comprising a sequence selected from the group consisting of SEQ ID NO 40, SEQ ID NO 41, SEQ ID NO 120, and SEQ ID NO 121.

69. The method of claim 68, wherein said first amplification oligonucleotide consists of the sequence of SEQ ID NO 39 and a sequence recognized by an RNA polymerase joined to the 5' end of SEQ ID NO 39; said second amplification oligonucleotide consists of either the sequence of SEQ ID NO 40 or SEQ ID NO 41; and said detection probe nucleotide base sequence consists of the sequence of SEQ ID NO 10.

70. The method of claim 16, wherein said nucleotide base sequence is selected from the group consisting of SEQ ID NO 11, SEQ ID NO 63, SEQ ID NO 77, and SEQ ID NO 91.

71. The method of claim 70, wherein said detection probe consists of an optionally labeled oligonucleotide, provided that the base sequence of said optionally labeled oligonucleotide consists of a detection probe nucleotide base sequence selected from the group consisting of SEQ ID NO 11, SEQ ID NO 63, SEQ ID NO 77, and SEQ ID NO 91.

72. The method of claim 71, wherein said detection probe comprises a reporter group label.

73. The method of claim 72, further comprising the step of amplifying HIV-1 nucleic acid, if present, using a first amplification oligonucleotide comprising a sequence selected from the group consisting of SEQ ID NO 42 and SEQ ID NO 122; and a second amplification oligonucleotide comprising a sequence selected from the group consisting of SEQ ID NO 43 and SEQ ID NO 123.

74. The method of claim 73, wherein said first amplification oligonucleotide consists of the sequence of SEQ ID NO 43 and a sequence recognized by an RNA polymerase joined to the 5' end of SEQ ID NO 43; said second amplification oligonucleotide consists of the sequence of SEQ ID NO 42; and said detection probe nucleotide base sequence consists of the sequence of SEQ ID NO 11.

75. The method of claim 16, wherein said nucleotide base sequence is selected from the group consisting of SEQ ID NO 12, SEQ ID NO 64, SEQ ID NO 78, and SEQ ID NO 92.

76. The method of claim 75, wherein said detection probe consists of an optionally labeled oligonucleotide, provided that the base sequence of said optionally labeled oligonucleotide consists of a detection probe nucleotide base sequence selected from the group consisting of SEQ ID NO 12, SEQ ID NO 64, SEQ ID NO 78, and SEQ ID NO 92.

77. The method of claim 76, wherein said detection probe comprises a reporter group label.

78. The method of claim 77, wherein said step (a) further comprises providing to said sample one or more helper oligonucleotides consisting of a nucleotide base sequence selected from the group consisting of SEQ ID NO 18, SEQ ID NO 98, SEQ ID NO 135, and SEQ ID NO 139.

79. The method of claim 77, further comprising the step of amplifying HIV-1 nucleic acid, if present, using a first amplification oligonucleotide comprising a sequence selected from the group consisting of SEQ ID NO 44 and SEQ ID NO 124; and a second amplification oligonucleotide comprising a sequence selected from the group consisting of SEQ ID NO 45 and SEQ ID NO 125.

80. method of claim 79, wherein said first amplification oligonucleotide consists of the sequence of SEQ ID NO 44 and a sequence recognized by an RNA polymerase joined to the 5' end of SEQ ID NO 44; said second amplification oligonucleotide consists of the sequence of SEQ ID NO 45; and said detection probe nucleotide base sequence consists of the sequence of SEQ ID NO 12.

81. The method of claim 16, wherein said nucleotide base sequence is selected from the group consisting of SEQ ID NO 13, SEQ ID NO 65, SEQ ID NO 79, and SEQ ID NO 93.

82. The method of claim 81, wherein said detection probe consists of an optionally labeled oligonucleotide, provided that the base sequence of said optionally labeled oligonucleotide consists of a detection probe nucleotide base sequence selected from the group consisting of SEQ ID NO 13, SEQ ID NO 65, SEQ ID NO 79, and SEQ ID NO 93.

83. The method of claim 82, wherein said detection probe comprises a reporter group label.

84. The method of claim 83, further comprising the step of amplifying HIV-1 nucleic acid, if present, using a first amplification oligonucleotide comprising a sequence selected from the group consisting of SEQ ID NO 46 and SEQ ID NO 126; and a second amplification oligonucleotide comprising a sequence selected from the group consisting of SEQ ID NO 47, SEQ ID NO 48, SEQ ID NO 50, SEQ ID NO 127, SEQ ID NO 128 and SEQ ID NO 130.

85. method of claim 84, wherein said first amplification oligonucleotide consists of the sequence of SEQ ID NO 46; said second amplification oligonucleotide consists of either the sequence of SEQ ID NO 47, SEQ ID NO 48, or SEQ ID NO 50; and said detection probe nucleotide base sequence consists of the sequence of SEQ ID NO 13.

86. The method of claim 16, wherein said nucleotide base sequence is selected from the group consisting of SEQ ID NO 14, SEQ ID NO 66, SEQ ID NO 80, and SEQ ID NO 94.

87. The method of claim 86, wherein said detection probe consists of an optionally labeled oligonucleotide, provided that the base sequence of said optionally labeled oligonucleotide consists of a detection probe nucleotide base sequence selected from the group consisting of SEQ ID NO 14, SEQ ID NO 66, SEQ ID NO 80, and SEQ ID NO 94.

88. The method of claim 87, further comprising the step of amplifying HIV-1 nucleic acid, if present, using a first amplification oligonucleotide comprising a sequence selected from the group consisting of SEQ ID NO 49 and SEQ ID NO 129; and a second amplification oligonucleotide comprising a sequence selected from the group consisting of SEQ ID NO 51 and SEQ ID NO 131.

89. method of claim 88, wherein said first amplification oligonucleotide consists of the sequence of SEQ ID NO 49; said second amplification oligonucleotide consists of the sequence of SEQ ID NO 51; and said detection probe nucleotide base sequence consists of the sequence of SEQ ID NO 14.

* * * * *